US011998026B2

(12) United States Patent
Gallop et al.

(10) Patent No.: US 11,998,026 B2
(45) Date of Patent: Jun. 4, 2024

(54) FRACTIONATED STILLAGE SEPARATION AND FEED PRODUCTS

(71) Applicant: ICM, Inc., Colwich, KS (US)

(72) Inventors: Charles C. Gallop, Gower, MO (US); Kurt A. Dieker, Wichita, KS (US); Christopher Riley William Gerken, Helena, MO (US); John A Pereira, St. Joseph, MO (US)

(73) Assignee: ICM, Inc., Colwich, KS (US)

( * ) Notice: Subject to any disclaimer, the term of this patent is extended or adjusted under 35 U.S.C. 154(b) by 717 days.

(21) Appl. No.: 16/624,831

(22) PCT Filed: Jun. 19, 2018

(86) PCT No.: PCT/US2018/038356
§ 371 (c)(1),
(2) Date: Dec. 19, 2019

(87) PCT Pub. No.: WO2018/236923
PCT Pub. Date: Dec. 27, 2018

(65) Prior Publication Data
US 2020/0113209 A1  Apr. 16, 2020

Related U.S. Application Data

(60) Provisional application No. 62/521,542, filed on Jun. 19, 2017.

(51) Int. Cl.
*A23K 10/10*        (2016.01)
*A23J 1/00*         (2006.01)
(Continued)

(52) U.S. Cl.
CPC ............... *A23K 10/10* (2016.05); *A23J 1/005* (2013.01); *A23J 1/12* (2013.01); *A23J 1/125* (2013.01);
(Continued)

(58) Field of Classification Search
CPC ........ A23K 10/10; A23K 10/38; A23K 40/00; A23K 50/10; A23K 50/30; A23K 50/75;
(Continued)

(56) References Cited

U.S. PATENT DOCUMENTS 2,217,264 A    10/1940  Charles
4,802,982 A    2/1989   Lien
(Continued)

FOREIGN PATENT DOCUMENTS

BR   112019027240-2   7/2020
BR   112019027367     7/2020
(Continued)

OTHER PUBLICATIONS

US 11,517,028 B2, 12/2022, Gallop et al. (withdrawn)
(Continued)

*Primary Examiner* — Liam Royce
(74) *Attorney, Agent, or Firm* — Schwegman Lundberg & Woessner, P.A.

(57) ABSTRACT

This disclosure describes methods to separate solids from liquids in a production facility. A process separates components in the process stream by applying non-condensable media to create density differences and then using a mechanical device to separate the solids from the liquids based on the density difference. The process produces the liquids and solids, which may be further processed to create valuable animal feed products.

6 Claims, 15 Drawing Sheets

(51) Int. Cl.
| | |
|---|---|
| *A23J 1/12* | (2006.01) |
| *A23J 1/16* | (2006.01) |
| *A23K 10/38* | (2016.01) |
| *A23K 40/00* | (2016.01) |
| *A23K 50/10* | (2016.01) |
| *A23K 50/30* | (2016.01) |
| *A23K 50/75* | (2016.01) |
| *A23K 50/80* | (2016.01) |
| *B01D 5/00* | (2006.01) |
| *B01D 17/02* | (2006.01) |
| *B01D 21/26* | (2006.01) |
| *B01D 61/14* | (2006.01) |
| *B03B 9/00* | (2006.01) |
| *C12N 1/16* | (2006.01) |

(52) U.S. Cl.
CPC ............... *A23J 1/16* (2013.01); *A23K 10/38* (2016.05); *A23K 40/00* (2016.05); *A23K 50/10* (2016.05); *A23K 50/30* (2016.05); *A23K 50/75* (2016.05); *A23K 50/80* (2016.05); *B01D 5/006* (2013.01); *B01D 17/0205* (2013.01); *B01D 17/0217* (2013.01); *B01D 21/26* (2013.01); *B01D 21/262* (2013.01); *B01D 21/267* (2013.01); *B01D 61/14* (2013.01); *B03B 9/00* (2013.01); *B01D 2311/2646* (2013.01); *B01D 2311/2676* (2013.01); *C12N 1/16* (2013.01); *Y02P 60/87* (2015.11)

(58) Field of Classification Search
CPC ....... A23K 50/80; B03D 1/1431; A23J 1/005; A23J 1/12; A23J 1/125; A23J 1/16; B01D 5/006; B01D 17/0205; B01D 17/0217; B01D 21/26; B01D 21/262; B01D 21/267; C12P 21/00; B03B 9/00; C12N 1/16; Y02P 60/87
See application file for complete search history.

(56) References Cited

U.S. PATENT DOCUMENTS

| | | | |
|---|---|---|---|
| 5,387,342 A * | 2/1995 | Rogers | B04B 1/04 210/512.3 |
| 8,962,059 B1 | 2/2015 | Froderman et al. | |
| 11,266,166 B2 | 3/2022 | Gallop et al. | |
| 11,553,726 B2 | 1/2023 | Gallop et al. | |
| 2005/0247647 A1 | 11/2005 | Hills | |
| 2005/0252858 A1 | 11/2005 | Peyton et al. | |
| 2006/0219635 A1 | 10/2006 | Mccague et al. | |
| 2007/0000769 A1* | 1/2007 | Brown | B01D 3/148 202/173 |
| 2008/0153149 A1 | 6/2008 | Van Leeuwen et al. | |
| 2009/0004712 A1 | 1/2009 | Rehkopf et al. | |
| 2010/0058649 A1 | 3/2010 | Bootsma | |
| 2011/0086149 A1 | 4/2011 | Bootsma | |
| 2011/0283602 A1 | 11/2011 | Gallop et al. | |
| 2011/0306485 A1 | 12/2011 | Kopper et al. | |
| 2012/0125859 A1 | 5/2012 | Collins et al. | |
| 2012/0183643 A1 | 7/2012 | Dale | |
| 2013/0121891 A1 | 5/2013 | Dieker et al. | |
| 2013/0130343 A1 | 5/2013 | Purtle et al. | |
| 2013/0165678 A1 | 6/2013 | Kohl et al. | |
| 2013/0206576 A1 | 8/2013 | Goel et al. | |
| 2013/0288376 A1 | 10/2013 | Lee | |
| 2013/0309738 A1 | 11/2013 | Barr et al. | |
| 2013/0344554 A1 | 12/2013 | Bleyer et al. | |
| 2014/0017728 A1 | 1/2014 | Bleyer et al. | |
| 2014/0147897 A1 | 5/2014 | Lee | |
| 2014/0206058 A1 | 7/2014 | Tewalt et al. | |
| 2014/0242251 A1 | 8/2014 | Bootsma | |
| 2014/0343259 A1 | 11/2014 | Bleyer et al. | |
| 2015/0118727 A1 | 4/2015 | Escudero et al. | |
| 2015/0152372 A1 | 6/2015 | Kohl et al. | |
| 2015/0164114 A1 | 6/2015 | Lee | |
| 2015/0191750 A1 | 7/2015 | Bleyer et al. | |
| 2015/0305370 A1 | 10/2015 | Bleyer et al. | |
| 2016/0152931 A1* | 6/2016 | Bootsma | C12M 47/10 426/624 |
| 2017/0015938 A1 | 1/2017 | Xiao et al. | |
| 2017/0051322 A1 | 2/2017 | Bushong et al. | |
| 2017/0253892 A1 | 9/2017 | Bootsma | |
| 2020/0113207 A1 | 4/2020 | Gallop et al. | |
| 2020/0128855 A1 | 4/2020 | Gallop et al. | |
| 2020/0139269 A1 | 5/2020 | Gallop et al. | |
| 2022/0183318 A1 | 6/2022 | Gallop et al. | |
| 2022/0248714 A1 | 8/2022 | Gallop et al. | |
| 2022/0378065 A1 | 12/2022 | Gallop et al. | |

FOREIGN PATENT DOCUMENTS

| | | |
|---|---|---|
| CA | 2763467 A1 | 12/2010 |
| CA | 2829480 | 9/2012 |
| CA | 2709247 | 9/2014 |
| CA | 3008883 A1 | 12/2018 |
| CA | 3166117 A1 | 12/2018 |
| CA | 3008883 C | 9/2022 |
| CN | 101386817 A | 3/2009 |
| CN | 105815574 A | 8/2016 |
| DE | 2748478 A1 | 5/1978 |
| EP | 3121258 A1 | 1/2017 |
| JP | 2009297665 A | 12/2009 |
| KR | 20140022589 A | 2/2014 |
| KR | 101598007 B1 | 2/2016 |
| WO | WO-2010138110 A1 | 12/2010 |
| WO | WO-2014209789 A1 | 12/2014 |
| WO | WO-2018236919 A2 | 12/2018 |
| WO | WO-2018236920 A2 | 12/2018 |
| WO | WO-2018236923 A2 | 12/2018 |
| WO | WO-2018236926 A2 | 12/2018 |

OTHER PUBLICATIONS

U.S. Appl. No. 16/624,824, Notice of Non-Compliant Amendment dated Jan. 12, 2023, 2 pgs.
U.S. Appl. No. 16/624,824, Response filed Oct. 25, 2022 to Non Final Office Action dated Jun. 2, 2022, 9 pgs.
U.S. Appl. No. 17/683,011, Corrected Notice of Allowability dated Oct. 13, 2022, 8 pgs.
U.S. Appl. No. 17/683,011, Corrected Notice of Allowability dated Dec. 8, 2022, 2 pgs.
U.S. Appl. No. 17/683,011, Examiner Interview Summary dated Sep. 26, 2022, 3 pgs.
U.S. Appl. No. 17/683,011, Notice of Allowance dated Sep. 29, 2022, 14 pgs.
Brazilian Application Serial No. 1120190272402, Office Action dated Sep. 8, 2022, w/ English Translation, 5 pgs.
Brazilian Application Serial No. 1120190272402, Response filed Dec. 19, 2022 to Office Action dated Sep. 8, 2022, w/ English Claims, 23 pgs.
Brazilian Application Serial No. 1120190273379, Office Action dated Sep. 8, 2022, w/ English translation, 6 pgs.
Brazilian Application Serial No. 1120190273670, Response filed Oct. 14, 2022 tow Office Action dated Jul. 4, 2022, w/ English claims, 79 pgs.
"U.S. Appl. No. 16/624,824, Non Final Office Action dated Jun. 2, 2022", 11 pgs.
"U.S. Appl. No. 16/624,824, Response filed Apr. 18, 2022 to Restriction Requirement dated Feb. 16, 2022", 6 pgs.
"U.S. Appl. No. 16/624,824, Restriction Requirement dated Feb. 16, 2022", 9 pgs.
"U.S. Appl. No. 17/672,493, Preliminary Amendment filed Aug. 22, 2022", 5 pgs.
"U.S. Appl. No. 17/683,011, Non Final Office Action dated Jun. 8, 2022", 19 pgs.
"U.S. Appl. No. 17/683,011, Response filed Sep. 7, 2022 to Non Final Office Action dated Jun. 8, 2022", 12 pgs.

(56) References Cited

OTHER PUBLICATIONS

"Argentina Application Serial No. P180101726, Office Action mailed May 9, 2022", w/ English translation, 7 pgs.
"Argentina Application Serial No. P180101726, Response filed Feb. 14, 2022 to Examination Report Demanding Clarifications Prior to Substantive Examination dated Nov. 4, 2021", w/ English claims, 78 pgs.
"Brazilian Application Serial No. 1120190273670, Office Action dated Jul. 4, 2022", w/ English Translation, 6 pgs.
"Ethanol co products", Iowa Renewable Fuels Association, [Online] Retrieved from the Internet: <URL: https://web.archive.org/web/20151003030131/http://iowarfa.org>, (2015), 6 pgs.
"Paraguay Application Serial No. 1847775, Office Action dated May 24, 2022", W/ English Translation, 9 pgs.
"Zeitsch (DE-2748478) original and machine translation attached", (1978), 20 pgs.
"International Application Serial No. PCT US2018 038353, International Preliminary Report on Patentability dated Jan. 2, 2020", 7 pgs.
"International Application Serial No. PCT US2018 038356, International Preliminary Report on Patentability dated Jan. 2, 2020", 10 pgs.
"International Application Serial No. PCT US2018 038352, International Preliminary Report on Patentability dated Jan. 2, 2020", 9 pgs.
"International Application Serial No. PCT US2018 038360, International Preliminary Report on Patentability dated Jan. 2, 2020", 8 pgs.
"Canadian Application Serial No. 3,008,874, Office Action dated Oct. 23, 2018", 4 pgs.
"Canadian Application Serial No. 3,000,874, Office Action dated Jan. 29, 2019", 3 pgs.
"Canadian Application Serial No. 3,000,874, Office Action dated May 7, 2019", 4 pgs.
"U.S. Appl. No. 16/624,836 Supplemental Preliminary Amendment", 8 pgs.
"U.S. Appl. No. 16/624,836, Notice of Allowance dated Nov. 2, 2021", 7 pages.
"Argentina Application Serial No. P180101726, Examination Report Demanding Clarifications Prior to Substantive Examination dated Nov. 4, 2021", with machine English translation, 9 pages.
International Application Serial No. PCT/US2018/038352, International Search Report dated Dec. 17, 2018, 3 pgs.
International Application Serial No. PCT/US2018/038352, Written Opinion dated Dec. 17, 2018, 7 pgs.
International Application Serial No. PCT/US2018/038353, International Search Report dated Jan. 28, 2019, 3 pgs.
International Application Serial No. PCT/US2018/038353, Written Opinion dated Jan. 28, 2019, 5 pgs.
International Application Serial No. PCT/US2018/038356, International Search Report dated Jan. 21, 2019, 3 pgs.
International Application Serial No. PCT/US2018/038356, Written Opinion dated Jan. 21, 2019, 8 pgs.
International Application Serial No. PCT/US2018/038360, International Search Report dated Jan. 21, 2019, 3 pgs.
International Application Serial No. PCT/US2018/038360, Written Opinion dated Jan. 21, 2019, 6 pgs.
Ratanapariyanuch, Kornsulee, et al., "Protein Concentrate Production from Thin Stillage", J. of Agricultural and Food Chemistry, vol. 64, No. 50, (2016), 9 pgs.
U.S. Appl. No. 16/624,811, Non Final Office Action dated Mar. 27, 2023, 23 pgs.
U.S. Appl. No. 16/624,824, Final Office Action dated Mar. 21, 2023, 11 pgs.
U.S. Appl. No. 16/624,824, Response filed Jan. 19, 2023 to Notice of Non-Compliant Amendment dated Jan. 12, 2023, 9 pgs.
Tsai, et al., "The effect of adding xylanase or β-glucanase to diets with corn distillers dried grains with solubles (CDDGS) on growth performance and nutrient digestibility in nursery pigs", Livestock Science. 197:46-52, (2017), 7 pgs.
Brazilian Application Serial No. 1120190272402, Response filed Oct. 31, 2023 to Office Action dated Aug. 8, 2023, w/ English claims, 11 pgs.
"U.S. Appl. No. 16/624,811, Response filed Jun. 21, 2023 to Advisory Action dated May 30, 2023", 15 pgs.
"U.S. Appl. No. 16/624,811, Response filed Jun. 27, 2023 to Non Final Action dated Mar. 27, 2023", 9 pgs.
"U.S. Appl. No. 16/624,811, Notice of Allowance dated Aug. 11, 2023", 14 pgs.
"U.S. Appl. No. 16/624,811, Corrected Notice of Allowability dated Aug. 31, 2023", 2 pgs.
"Paraguay Application Serial No. 1847775, Office Action dated Jun. 29, 2023", w/ English Machine Translation, 16 pgs.
"Brazilian Application Serial No. 1120190272402, Office Action dated Aug. 8, 2023", w/ English Machine Translation, 6 pgs.
U.S. Appl. No. 16/624,824, Non Final Office Action dated Sep. 20, 2023, 10 pgs.
Brazil Application Serial No. 1120190273379, Opinion for non-patenteability (RPI 7.1) dated Sep. 8, 2023, W/O English Translation, 4 pgs.
Canadian Application Serial No. 3,008,883, Office Action dated Jan. 4, 2019, 3 pgs.
Canadian Application Serial No. 3,008,883, Office Action dated Jan. 11, 2021, 3 pgs.
Canadian Application Serial No. 3,008,883, Office Action dated Jul. 6, 2020, 3 pgs.
Canadian Application Serial No. 3,008,883, Office Action dated Jul. 19, 2021, 3 pgs.
Canadian Application Serial No. 3,008,883, Office Action dated Sep. 19, 2019, 5 pgs.
Canadian Application Serial No. 3,008,883, Response filed Mar. 19, 2020 to Office Action dated Sep. 19, 2019, 21 pgs.
Canadian Application Serial No. 3,008,883, Response filed May 11, 2021 to Office Action dated Jan. 11, 2021, 15 pgs.
Canadian Application Serial No. 3,008,883, Response filed Jul. 4, 2019 to Office Action dated Jan. 4, 2019, 14 pgs.
Canadian Application Serial No. 3,008,883, Response filed Nov. 6, 2020 to Office Action dated Jul. 6, 2020, 17 pgs.
Canadian Application Serial No. 3,008,883, Response filed Nov. 19, 2021 to Office Action dated Jul. 19, 2021, 15 pgs.
Canadian Application Serial No. 3,166,117, Response filed Sep. 11, 2023 to Examiners Rule 86(2) Report dated May 12, 2023, 14 pgs.
Canadian Application Serial No. 3,166,117, Examiners Rule 86(2) Report dated Sep. 21, 2023, 4 pgs.
U.S. Appl. No. 16/624,811, Notice of Allowance dated Nov. 24, 2023, 16 pgs.
U.S. Appl. No. 16/624,824, Response filed Dec. 20, 2023 to Non Final Office Action dated Sep. 20, 2023, 12 pgs.
Brazil Application Serial No. 1120190273379, Response filed Dec. 15, 2023 to Opinion for non-patentability (RPI 7.1) dated Sep. 8, 2023, 7 pgs.

\* cited by examiner

FRACTIONATED STILLAGE SEPARATION AND FEED PRODUCTS

CROSS REFERENCE TO RELATED APPLICATION

This application is a U.S. National Stage Filing under 35 U.S.C. 371 from International Application No. PCT/US2018/038356, filed on Jun. 19, 2018, and published as WO 2018/236923 A1 on Dec. 27, 2018, which claims the benefit of priority to U.S. Provisional Application No. 62/521,542, filed on Jun. 19, 2017, the content of each of which is hereby incorporated by reference in its entirety.

TECHNICAL FIELD

The subject matter of this disclosure relates to methods of separating a fractionated stillage process stream in a production facility for biofuels and producing valuable feed products from these methods. In particular, the subject matter is directed to using at least one mechanical device to separate components in the fractionated stillage process stream and to recover the various components to produce valuable feed products. These methods help remove suspended solids, recover components, reduce the amount of energy needed for downstream processing, reduce greenhouse gas emissions and/or carbon emissions, and increase overall efficiency of a process in the production facility.

BACKGROUND

The United States relies on imported petroleum to meet the needs of transportation fuel. To reduce dependence on the imported petroleum, the Environmental Protection Agency (EPA) set standards for a Renewable Fuel Standard (RFS) program each year. The RFS is a national policy that requires a mandate to blend renewable fuels into transportation fuel, which ensures the continued growth of renewable fuels. The RFS proposes annual standards for four types of renewable fuels, such as cellulosic biofuel, biomass-based diesel, advanced biofuel, and total renewable fuel to replace or to reduce the quantity of gasoline and diesel. The new RFS2 proposal is for 36 billion gallons of renewable fuel to be produced and for consumption by 2022, which is retrieved from the U.S. EPA website under RFS Program on Apr. 28, 2017.

The RFS2 has also added explicit definitions for renewable fuels to qualify as renewable biomass, to reduce greenhouse gas (GHG) emissions by certain percentage, to improve vehicle efficiency, and to be cleaner, lower-carbon fuels. The EPA created a Lifecycle analysis, which may be referred to as fuel cycle or well-to-wheel analysis. The Lifecycle analysis is to assess the overall GHG impacts of a fuel, including each stage of its production and use. EPA's Lifecycle analysis includes significant indirect emissions as required by the Clean Air Act.

Other efforts have focused on establishing a national low carbon fuel standard (LCFS) together. The LCFS includes all types of transportation fuels (i.e., electricity, natural gas, hydrogen, and biofuels), requires reducing a fuel's average life-cycle GHG emissions or carbon-intensity (CI) over a certain period of time, and stimulates innovation by rewarding production facilities that reduce GHG or carbon emissions at every step. Production facilities can reduce CI of fuels by selling more low-carbon fuels, reducing the CI of fossil fuels, improving efficiencies, reducing carbon footprints, capturing and sequestering carbon, and/or purchasing credits from other producers who are able to supply low-carbon fuels at lower prices. California and some countries have adopted the LCFS policy. Other states and regions in the U.S. are considering adopting a LCFS policy similar to California's model.

A national LCFS would affect the economy and environment. These effects may be based on cost and availability of low-carbon fuels, GHG timeline reduction, and creation of a credit system. Advantages of incorporating LCFS to RFS2 are to reduce transportation fuel consumption and lower fuel prices, lower crop prices by shifting toward cellulosic feedstocks, and reduce GHG or carbon emissions significantly domestically and globally. Thus, production facilities are seeking ways to implement LCFS on their own.

It is desirable to find methods to reduce GHG emissions and/or to reduce CI, which includes finding more efficient technologies. For instance, there are known techniques to separate solids from liquids in process streams. However, these techniques are not very efficient. For instance, one method uses gravity separation with the process streams to separate and to recover various components. Problems are that gravity separation may not separate components very well and requires a long time.

Other methods may not adequately separate solids from liquids in the process streams, are very expensive to operate, require frequent maintenance and repair, and require a higher skill set to operate and to maintain. The process streams may contain high amounts of solids that cause fouling of the evaporators. Also, the solids may have high moisture content, which increases the operating costs to transport and to dry the solids downstream. The equipment may create high levels of emissions from the plants, as well as increase capital and operating costs. Moreover, none of the above methods may be easily integrated into a production facility or capitalize on producing products and feed products.

Accordingly, there are needs for separating solids from liquids in an efficient manner and needs to increase value from products. The methods described are improved mechanisms for separating components in a fractionated stillage process stream and creating valuable animal feed products in a more efficient manner.

SUMMARY

This disclosure describes methods for separating components in a fractionated stillage process stream by enhancing solid-liquid separation and recovering the components to produce valuable animal feed products, while improving overall efficiency. This disclosure helps to reduce an amount of energy needed for downstream processing, which in turn reduces GHG or carbon emissions, decreases the amount of energy used for downstream processing and reduces operating costs and/or reduces capital costs, which in turn may lower biofuel costs.

In an embodiment for reducing an amount of energy needed for processing streams, a process separates components in a fractionated stillage process stream by adding non-condensable media to the fractionated stillage process stream to reduce density of liquids relative to the density differential to suspended solids and by using a mechanical device to separate the suspended solids from the liquids, where the density differences assist with the mechanical separation. The process further produces the solids to be used as a wet feed product, dries the solids to create a dried feed product, and further sends the liquids to evaporators to create a dried syrup product.

In another embodiment for reducing an amount of energy needed for processing streams, a process separates components in a process stream. The process sends the process stream through a first separation device, which creates a heavy phase with suspended solids and a light emulsion phase with dissolved solids. Next, the process sends the heavy phase with suspended solids to a second separation device, which creates two components of a clarified heavy phase with solids and a light phase concentrate.

In another embodiment for reducing the amount of energy needed for processing streams, a process separates components in a process stream by adding non-condensable media to the process stream to reduce density of liquids relative to the density differential to suspended solids. Next, the process uses a mechanical device with g forces to separate the suspended solids from the liquids.

In yet another embodiment for creating valuable feed products, the process receives a process stream. The process adds an organism to the process stream, sends to evaporator and dries the material to create valuable livestock (i.e., monogastric) and aqua feed product.

In an embodiment, a composition of the feed products includes dry matter ranging from about 45% to about 80%, protein ranging from about 10% to about 20%, and potassium ranging from about 2% to about 8%.

In another embodiment, a composition of the animal feed products includes dry matter ranging from about 70% to about 95%, protein ranging from about 35% to about 55%, and neutral detergent fiber ranging from about 20%/to about 50%.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The features illustrated in the figures are not necessarily drawn to scale, and features of one embodiment may be employed with other embodiments or features may not be employed in all embodiments as the skilled artisan would recognize, even if not explicitly stated herein.

DETAILED DESCRIPTION

Overview

Figure 1:
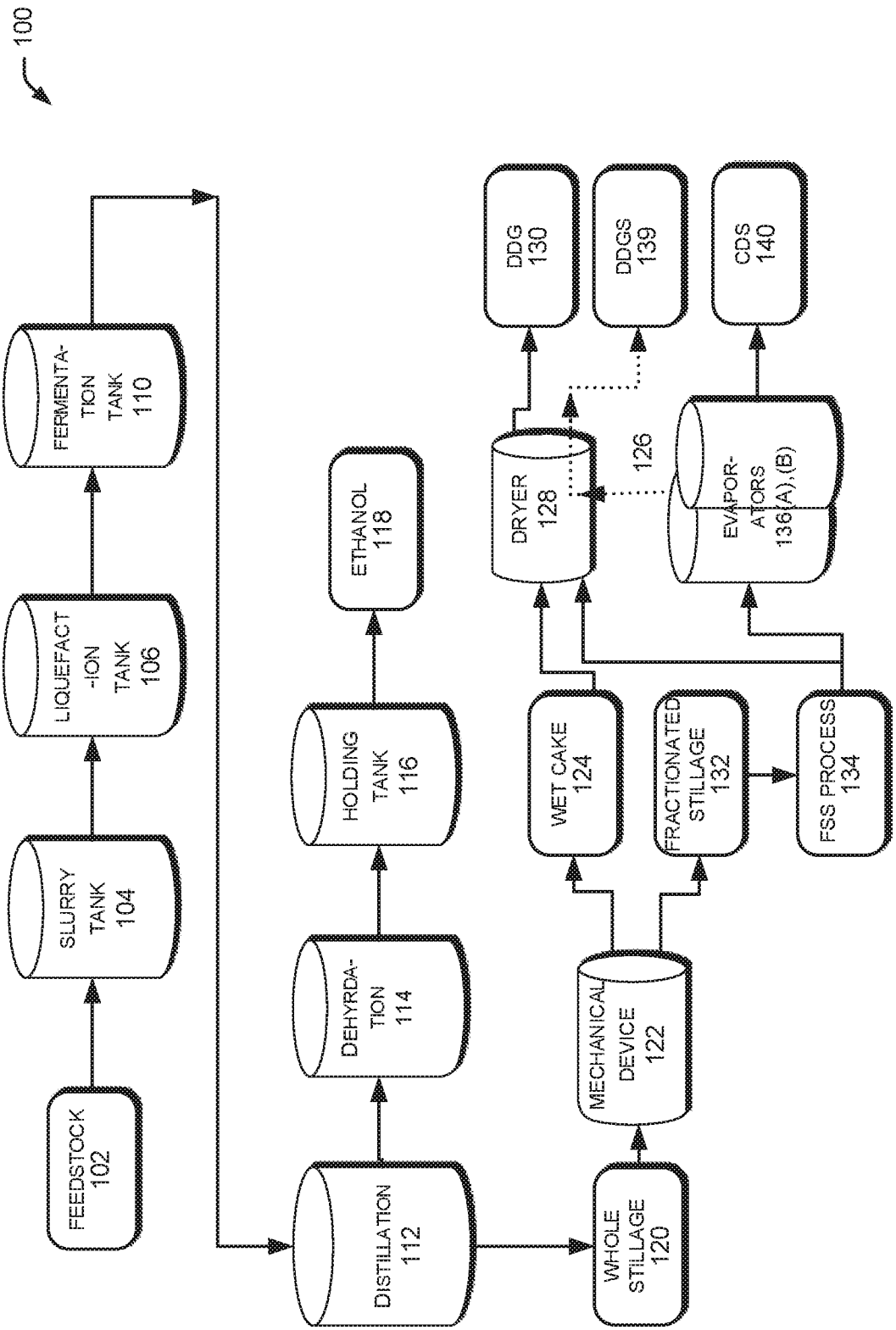
FIGS. 1 and 2 illustrate example environments for a fractionated stillage separation (FSS) process in a production facility.

The Detailed Description explains embodiments of the subject matter and the various features and advantageous details more fully with reference to non-limiting embodiments and examples that are described and/or illustrated in the accompanying figures and detailed in the following attached description. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter.

This disclosure describes environments and techniques for FSS processes by separating solids from liquids in a process stream, which may be obtained from a production facility. For instance, the production facility may include, but is not limited to, biofuels, alcohol, animal feed, oil, biodiesel, pulp and paper, textile, chemical industry, and other fields. Removal of liquids from the solids will increase the concentration of solids in downstream process streams, enhance more efficient solid-liquid separation to recover components, and allow more efficient drying for downstream processing.

The FSS process presents opportunities to reduce GHG or carbon emissions by providing methods to produce solids having less moisture or higher solids content than conventional methods. With the solids having less moisture or higher solids content, the process may reduce energy usage downstream for drying and/or evaporating and reduce operating costs while improving efficiency in the production facility. For instance, the downstream processing uses electricity and natural gas to operate the evaporators and dryers, which generate emissions into the atmosphere. With the FSS process, the amount of electricity and natural gas to operate the evaporators and dryers would be reduced and so would the amount of emissions.

Furthermore, the FSS process provides biofuels that have a lower carbon intensity than conventional biofuels or hydrocarbon fuels. For instance, the LCFS establishes carbon intensity standard measured in grams $CO_2$ equivalent per mega-joule of fuel energy ($gCO_2e/MJ$) over a certain period of time. The production facilities supply an accounting of net fuel emissions per unit of fuel energy. It appears that the FSS process operates within regulatory agencies that can quantify environmental benefits or associate a biofuel or a tradable credit. Thus, there are economic incentives, environmental benefits, other advantages, and benefits to using the FSS process that provide a more energy efficient industrial process.

The FSS process produces valuable feed products and co-products. The feed products may include, but are not limited to, Distiller's Dried Grains with Solubles (DDGS), Condensed Distillers Solubles (CDS), Single Cell Protein (SCP), UltraMax™, SolMax™, grain distillers dried yeast, syrup with fiber, and the like. The co-products may also include, but are not limited to, corn distillers oil, clarified products, and/or concentrated products.

One embodiment may be for reducing the amount of energy needed for processing streams, by separating the components in a process stream with using at least one mechanical device to create separate components for further processing. Another embodiment may include separating the components in a process stream with using at least two devices to create the separate components to create co-products.

Embodiments of the FSS process are shown for illustration purposes in the dry grind process. The FSS process may be implemented in the different fields as discussed above. While aspects of described techniques can be implemented in any number of different environments, and/or configurations, implementations are described in the context of the following example processes. There may be fewer equipment, chemical, enzymes, or processes needed in the subject matter, than shown in the following example process figures.

Illustrative Environments

Figure 2:
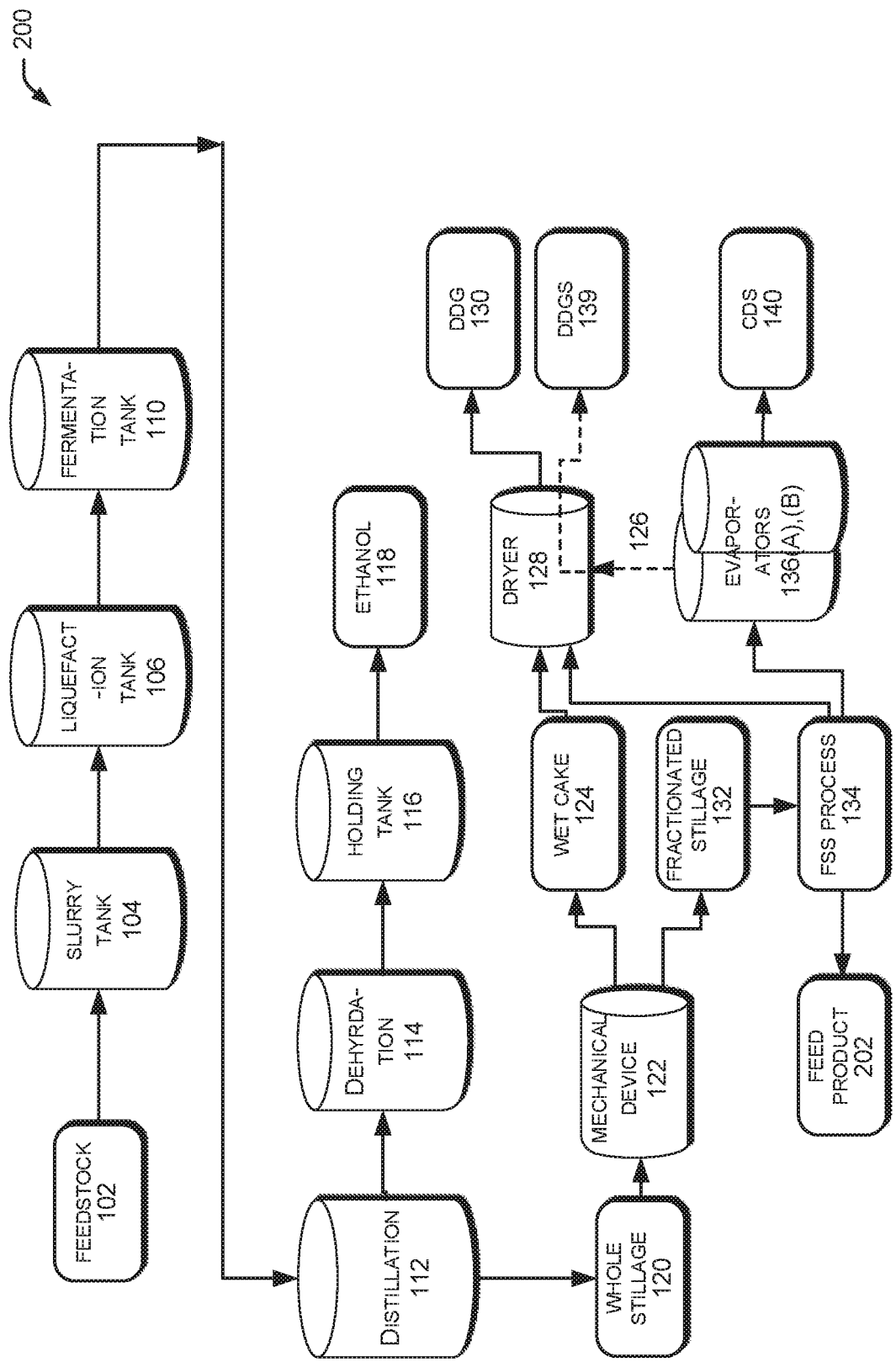

FIGS. 1-2 are flow process diagrams showing example environments that may be used with the FSS process. The process may be performed using a combination of different environments and/or types of equipment. Any number of the described environments, processes, or types of equipment may be combined in any order to implement the method, or an alternate method. There may be less or more equipment than shown and may be in any order. Moreover, it is also possible for one or more of the provided steps or pieces of equipment, chemical, enzymes, or other processes to be omitted.

FIG. 1 illustrates an example of a process 100 implementing a series of operations in a dry grind mill of an alcohol production facility. The process 100 in the dry grind mill may operate in a continuous manner. In other implementations, the process 100 may operate in a batch process or a combination of batch and continuous processes.

The process 100 may receive feedstock of a grain that includes, but is not limited to, barley, beets, cassava, corn, cellulosic feedstock, grain, milo, oats, potatoes, rice, rye, sorghum grain, triticale, sweet potatoes, lignocellulosic biomass, wheat, and the like, or pulp. Lignocellulosic biomass may include corn fiber, corn stover, corn cobs, cereal straws, sugarcane bagasse and dedicated energy crops, which are mostly composed of fast growing tall, woody grasses, including, but not limited to, switch grass, energy/forage sorghum, miscanthus, and the like. Also, the feedstock may further include, grain fractions or by-products as produced by industry, such as hominy, wheat middlings, corn gluten feed, Distillers Dried Grains with Solubles, and the like. The feedstock may include, an individual type, a combined feedstock of two types, of multiple types, or any combination or blend of the above grains. The feedstock may include, but is not limited to, one to four different types combined in various percentage ranges. The feedstock may be converted into different products and co-products that may include, but is not limited to, ethanol, syrup, distillers oil, distillers dried grains, distillers dried grains with solubles, condensed distillers solubles, wet distillers grains, and the like. For instance, a bushel of corn may produce about 17-19 pounds of ethanol, about 17-18 pounds of DDGS and 17-18 pounds of carbon dioxide. The carbon dioxide can be captured and compressed into liquid carbon dioxide or dry ice for commercial applications.

For brevity purposes, the process 100 of using a single stream of feedstock will be described with reference to FIG. 1. As an example, corn may be used as a single feedstock in the dry grind process. Corn may be broken down into its major components of endosperm, germ, bran, and tip cap. Each of these major components may be further broken down to their smaller components. The endosperm, the germ, the bran, and the tip cap each contains varying amounts of starch, protein, oil, fiber, ash, sugars, etc. For instance, the amounts of the components in corn may include, but are not limited to, about 70 to 74% starch, about 7 to 9% protein, about 3 to 4% oil, about 7 to 9% fiber, about 1 to 2% ash, about 1 to 2% sugars, and others.

One skilled in the art understands that inspecting and cleaning of the corn occurs initially. At feedstock 102, the process 100 initially grinds the feedstock 102 into a meal, a powder, or a flour to achieve an appropriate particle size. The process 100 may grind the feedstock 102 by using hammer mills or roller mills. This grinding serves to break an outer coating of the corn kernel and increases a surface area to expose starch for penetration of water in cooking.

In an embodiment, the process 100 grinds the feedstock 102 with a hammer mill (not shown) to create a meal, a powder, a flour or a ground material. The hammer mill is a cylindrical grinding chamber with a rotating drum, flat metal bars, and a screen. The screen size may be, but is not limited to, 4/64 to 12/64 inch hole sizes. An example hammer mill may have screen openings that are sized 7/64 inch, or about 2.78 millimeters (mm) to create small particles that are sized about 0.5 to about 2-3 mm.

In another embodiment, the process 100 grinds the feedstock 102 with a roller mill (not shown) to create a meal, a powder, a flour or a ground material. The roller mill receives the feedstock 102, sends the feedstock 102 between two or more rolls or wheels, and crushes the feedstock 102 to create ground material. One roll may be fixed in position while the other roll may be moved further or closer towards the stationary roll. The roll surfaces may be grooved to help in shearing and disintegration of the corn. The example rolls may be about 9 to about 12 inches (23 to 30.5 cm) in diameter, with a ratio of length to diameter that may be about 4:1. The small particles may be sized about 0.5 to about 2-3 mm.

The process 100 sends the ground material to a slurry tank 104. Next, the process 100 adds water, backset, and enzymes to the feedstock 102 that has been ground to create a slurry in the slurry tank 104. In an example, the process 100 adds a liquefying enzyme, such as alpha-amylase to this mixture. The alpha-amylase enzyme hydrolyzes and breaks starch polymer into short sections, dextrins, which are a mix of oligosaccharides. The process 100 maintains a temperature between about 60° C. to about 100° C. (about 140° F. to about 212° F., about 333 K to about 373 K) in the slurry tank 104 to cause the starch to gelatinize and a residence time of about 30 to about 60 minutes to convert insoluble starch in the slurry to soluble starch. The slurry may have suspended solids content of about 26% to about 40%, which includes starch, fiber, protein, and oil. Other components in the slurry tank 104 may include, grit, salts, and the like, as is commonly present on raw incoming grain from agricultural production, as well as recycled waters that contain acids, bases, salts, yeast, and enzymes. The process 100 adjusts the pH of the slurry to about 4.5 to 6.0 (depending on enzyme type) in the slurry tank 104.

In an embodiment, the slurry may be heated to further reduce viscosity of the ground grain. The parameters include heating for longer periods and/or at higher temperatures. In some embodiments, there may be two or more slurry tanks used for an additional residence time and a viscosity reduction.

In an embodiment, the process 100 pumps the slurry to jet cookers (not shown) to cook the slurry. Jet cooking may occur at elevated temperatures and pressures. For example, jet cooking may be performed at a temperature of about 104° C. to about 150° C. (about 220° F. to about 302° F.) and at an absolute pressure of about 1.0 to about 6.0 kg/cm$^2$ (about 15 to 85 lbs/in$^2$) for about five minutes. Jet cooking is another method to gelatinize the starch.

The process 100 sends the slurry to liquefaction tank 106, which converts the slurry to mash. The process 100 uses a temperature range of about 80° C. to about 150° C. (about 176° F. to about 302° F., about 353 K to about 423 K) to hydrolyze the gelatinized starch into maltodextrins and oligosaccharides to produce a liquefied mash. Here, the process 100 produces a mash stream, which has about 26% to about 40% total solids content. The mash may have suspended solids content that includes protein, oil, fiber, grit, and the like. In embodiments, one or more liquefaction tanks may be used in the process 100.

The process 100 may add another enzyme, such as glucoamylase in the liquefaction tank 106 to break down the dextrins into simple sugars. Specifically, the glucoamylase enzyme breaks the short sections into individual glucose. The process 100 may add the glucoamylase enzyme at about 60° C. (about 140° F., about 333 K) before fermentation starts, known as saccharification, or at the start of a fermentation process. In an embodiment, the process 100 further adjusts the pH to about 5.0 or lower in the liquefaction tank 106. In another embodiment, saccharification and fermentation may also occur simultaneously.

At liquefaction tank 106, the process 100 obtains the process stream or a mixture from the slurry tank 104. In other embodiments, the process 100 may obtain a process stream or mixture as slurry from a slurry tank, from a jet cooker, from a first liquefaction tank, from a second liquefaction tank, or after a pretreatment process in cellulosic production facility.

At fermentation tank 110, the process 100 adds a microorganism to the mash for fermentation in the fermentation tank 110. The process 100 may use a common strain of microorganism, such as *Saccharomyces cerevisiae* to convert the simple sugars (i.e., maltose and glucose) into alcohol with solids and liquids, $CO_2$, and heat. The process 100 may use a residence time in the fermentation tank 110 as long as about 50 to about 60 hours. However, variables such as a microorganism strain being used, a rate of enzyme addition, a temperature for fermentation, a targeted alcohol concentration, and the like, may affect fermentation time. In embodiments, one or more fermentation tanks may be used in the process 100.

The process 100 creates alcohol, solids, liquids, microorganisms, and various particles through fermentation in the fermentation tank 110. Once completed, the mash is commonly referred to as beer, which may contain about 10% to about 20% alcohol, plus soluble and insoluble solids from the grain components, microorganism metabolites, and microorganism bodies. The microorganism may be recycled in a microorganism recycling step, which is an option. The part of the process 100 that occurs prior to distillation 112 may be referred to as the "front end", and the part of the process 100 that occurs after distillation 112 may be referred to as the "back end".

Turning to distillation 112, the process 100 distills the beer to separate the alcohol from the non-fermentable components, solids and the liquids by using a distillation process, which may include one or more distillation columns, beer columns, and the like. The process 100 pumps the beer through distillation 112, which is boiled to vaporize the alcohol or produce concentrated stillage. The process 100 condenses the alcohol vapor in distillation 112 where liquid alcohol exits through a top portion of the distillation 112 at about 90% to about 95% purity ethanol, 5% water which is about 190 proof. In embodiments, the distillation columns and/or beer columns may be in series or in parallel.

At dehydration 114, the process 100 removes any moisture from the 190 proof alcohol by going through dehydration. The dehydration 114 may include one or more drying column(s) packed with molecular sieve media to yield a product of nearly 100% alcohol, which is 200 proof alcohol.

At holding tank 116, the process 100 adds a denaturant to the alcohol. Thus, the alcohol is not meant for drinking, but to be used for motor fuel purposes. At 118, an example product that may be produced is ethanol, to be used as fuel or fuel additive for motor fuel purposes.

At 120, the water-rich product remaining from the distillation 112 is commonly referred to as whole stillage. The components in the whole stillage 120 may include but are not limited to, starches, soluble organic and inorganic compounds, suspended solids containing protein, carbohydrate, dissolved solids, water, oil, fat, protein, fiber, minerals, acids, bases, recycled yeast, non-fermented carbohydrates, by-products, and the like. Whole stillage 120 falls to the bottom of the distillation 112 and passes through a mechanical device 122.

The mechanical device 122 separates the whole stillage 120 to produce wet cake 124 (i.e., insoluble solids) and fractionated stillage 132 (i.e., aqueous liquids). The mechanical device 122 may include, but is not limited to, a centrifuge, a decanter, or any other type of separation device. The mechanical device 122 may increase solids content from about 10% to about 15% total solids to about 25% to about 40% total solids. There may be one or more mechanical devices in a series.

The wet cake 124 is primarily solids, which may be referred to as Distillers Wet Grains (DWG; Association of American Feed Control Officials (AAFCO) 2017 Official Publication at 27.8). This includes, but is not limited to, protein, fiber, fat, and liquids. DWG may be stored for less than a week to be used as feed for cattle, pigs, or chicken. The process 100 may transfer some of the wet cake 124 to one or more dryer(s) 128 to remove liquids. The dryer 128 capacity may be a bottleneck for a plant. This drying produces Distillers Dried Grains (DDG) 130 (AAFCO 2017 Official Publication at 27.5), which has a solids content of about 88% to 90% and may be stored indefinitely to be used as feed.

Returning to the fractionated stillage 132, the composition of the fractionated stillage 132 is mostly liquids left over from whole stillage 120 after being processed in the mechanical device 122. The fractionated stillage 132 may include oils, fibers, yeast, metabolic byproducts, non-fermentable solids, and the like. The fractionated stillage 132 may range from about 3% to about 12% by weight of total solids, which includes about 3% to about 7% dissolved solids about 1% to about 5% of the suspended solids. Total solids refer to components in a process stream other than water. This is used in reference to total solids, by weight. Dissolved solids refer to solids particles mixed sufficiently with fluid in process stream so they do not separate from the process stream during processing. The suspended solids refer to process stream containing suspended solids particles which can be separated from the process stream. The particle size in the suspended solids may include 20 micrometers in diameter, some may be smaller or larger.

The fractionated stillage 132 needs further processing due to its total solids composition. The process 100 sends the fractionated stillage 132 through the FSS process 134. For illustrative purposes in FIG. 1, the FSS process 134 is presented at a high level in a back end of the production facility. Details of embodiments of the FSS process 134 will be discussed later with reference to FIGS. 3-12. The FSS process 134 may be included with any process as part of the dry grind process or any type of process in a production facility. Specifically, the FSS process 134 helps to improve the separation of solids from liquids in an efficient manner, improve evaporator operation, increase throughput, provide feed streams for further processing to produce valuable animal feed products and/or oil, and to reduce GHG or carbon emissions. The animal feed products may be feed to ruminants (i.e., beef and dairy cattle), non-ruminants (i.e., pigs, chickens), and aqua-culture species.

The process 100 sends a stream to the evaporators 136 (A)(B) to boil away liquids from the fractionated stillage 132. This creates a thick syrup 126 (i.e., about 25% to about 50% dry solids), which contains soluble or dissolved solids, suspended solids (generally less than 50 µm) and buoyant suspended solids from fermentation.

The evaporators 136(A), (B) may represent multiple effect evaporators, such as any number of evaporators, from one to about twelve evaporators. Some process streams may go through a first effect evaporator(s) 136(A), which includes one to four evaporators and operates at higher temperatures, such as ranging to about 210° F. (about 99° C. or about 372 K). While other process streams may go through a second effect evaporator(s) 136(B), which operates at slightly lower temperatures than the first effect evaporator(s) 136(A), such as ranging from about 130° F. to about 188° F. (about 54° C. to about 87° C. or about 328 K to about 360 K). The second effect evaporator(s) 136(B) may use heated vapor from the first effect evaporator(s) 136(A) as heat or use recycled steam. In other embodiments, there may be three or four effect evaporator(s), which operate at lower temperatures than the second effect evaporator(s). In embodiments, the multiple effect evaporators may range from one effect up to ten effects or more. This depends on the plants, the streams being heated, the materials, and the like. In embodiments, the evaporators may be in series or in parallel.

The process 100 sends the syrup 126 from the evaporators 136(A), (B) to become combined with wet cake in the dryer 128 to produce Distillers Dried Grains with Solubles (DDGS) 139 (AAFCO 2017 Official Publication at 27.5) or could be left wet. However, the fractionated stillage 132 could contain high amounts of suspended solids. Thus, the fractionated stillage 132 with the high amounts of suspended solids may cause efficiency problems in the evaporators. Furthermore, this processing step of evaporating to concentrate solids in high water content streams requires a significant amount of energy. Thus, the amount of energy required increases the operating costs. The evaporator capacity may be a bottleneck in the plant.

In another embodiment, the process 100 sends the syrup 126, which is concentrated having about 20% to about 45% by weight of total solids, to be sold as Condensed Distillers Solubles (CDS) 140 (AAFCO 2017 Official Publication at 27.7). This is sold at a very low price. The CDS 140 may contain fermentation by-products, moderate amounts of fat, spent yeast cells, phosphorus, potassium, sulfur and other nutrients. The moisture content for the CDS 140 may range from about 55% to about 80%.

In another embodiment, the process 100 may send stream from the evaporators 136 (A), (B) to a process for oil recovery, which removes oil from the fractionated stillage 132 to recover oil. As a result, the process 100 produces a product of back-end oil and solids. The process 100 may send solids, water, and the like from the oil recovery back to the evaporators 136 (A), (B) for further processing.

FIG. 2 is similar to FIG. 1, except this figure illustrates another embodiment of the FSS process 134. The process 200 illustrates the production of Feed Product 202 from the FSS process 134. The Feed Products produced are described with details with reference to FIGS. 4, 5, and 9-15. Other embodiments may include the FSS process being located after whole stillage or after any of the evaporators (i.e., after one, two, three, last, and the like).

Examples of FSS Processes

Figure 3:
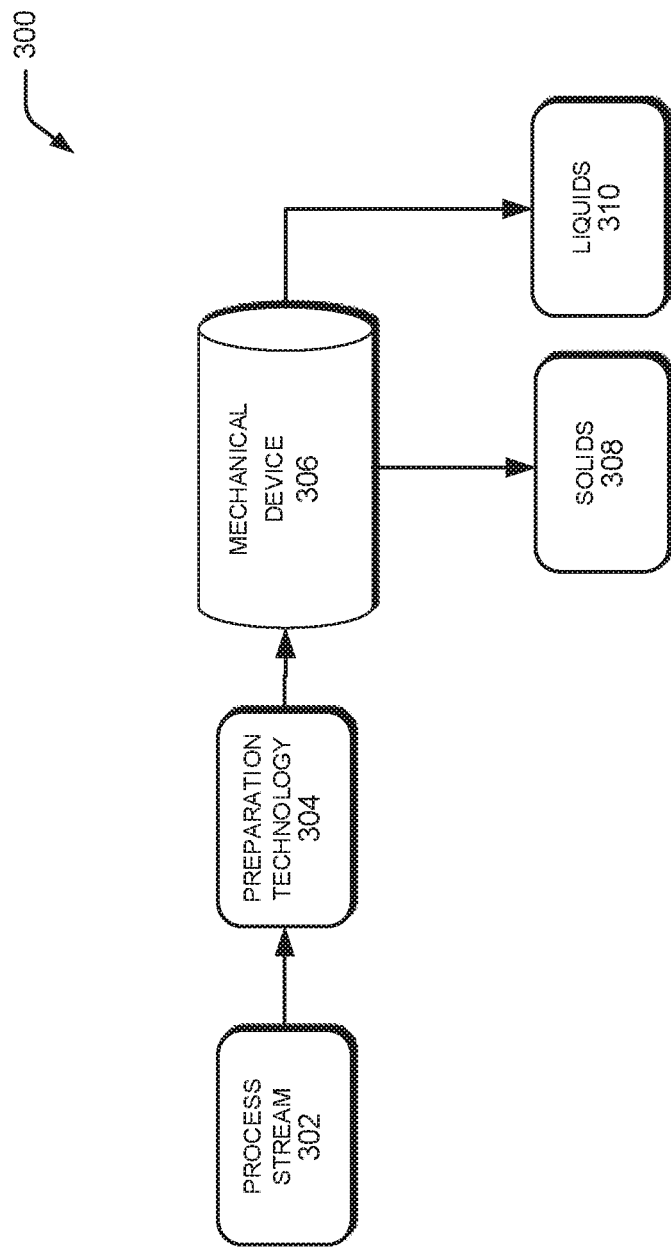
FIGS. 3-5 illustrate examples of FSS processes using a preparation technology and a mechanical device to separate solids from liquids.

FIGS. 3-12 illustrate examples of the FSS processes that may be used with the various environments described in this specification. FIG. 3 illustrates a preferred embodiment of the FSS process 300, which acts on a process stream 302 that includes a mixture of one or more solids and one or more liquids. For example, the process stream 302 can be a stream that includes a mixture of one or more solids and one or more liquids from a production facility, such as from the example processes 100 and 200 of FIGS. 1 and 2. In an example, the process stream 302 is the fractionated stillage 132 from process 100 or process 200, which is separated from a wet cake 124 by a mechanical device 122. Those of skill in the art will appreciate that other possible process streams may include, but are not limited to, whole stillage, centrate, thin stillage, mid stillage, backset, post liquefaction dilution, syrup, any type of process streams or mixtures in any type of production facilities, and the like. The process stream 302 may comprise about 4% to about 12% total solids, which may include about 3% to about 7% dissolved solids and about 1% to about 5% suspended solids (i.e., insoluble solids). The amount of fat in the process stream 302 may range from about 12% to about 37% fat and range from around 10% to about 30% protein.

The FSS process 300 applies a preparation technology 304 to be used with a mechanical device 306 to provide a separated solids stream 308 (also referred to simply as "solids 308" and a separated liquids stream 310 (also referred to simply as "liquids 310"). The preparation technology 304 may include non-condensable media, including, but not limited to, air or oxygen, carbon dioxide, nitrogen, other gases, and the like, which may be compressed or not. Other gases may include but are not limited to, hydrogen, helium, argon, and neon group Members in the Group 16/VIA, referred to as chalcogens, have similar properties, such as sulfur and selenium are the next two elements in the group, and they react with hydrogen gas ($H_2$) in a manner similar to oxygen. Air may be composed of 78% of nitrogen, 21% oxygen and with lesser amounts of argon, carbon dioxide, and other gases. The process 300 adds the preparation technology 304 to the process stream 302 through online injection, diffusers, or aeration, which causes the liquids to have a lower density than the solids. The density differential of the liquids 310 relative to the solids 308 assist in the separation efficiency of the mechanical device 306.

The mechanical device 306 may be any type of dynamic or static mechanical processor that separates out heavier suspended solids from other lighter solids, solids from liquids, and the like. The mechanical device 306 may include, but is not limited to, a sedicanter, a decanter centrifuge, a disk stack centrifuge, a cyclone, a hydrocyclone, a settling tank, filtration devices, and the like. The type of mechanical device 306 to be used depends on factors, such as type of process streams, liquid and solid goals at start and at end of process, the type of solids, density of materials, desired reduction of carbon intensity, desired reduction of GHG emissions, and the like.

In an embodiment, the mechanical device 306 may be a sedicanter, such as Flottweg's Sedicanter® S6E, which provides centrifugal force between 3,000 and 10,000×g for an efficient separation and clarification. The centrifugal force is generated by rotation. The Sedicanter® is rectangular shaped having a conveyer scroll located inside a bowl, both rotating at slightly different speeds. The solids and liquids travel in the same direction (co-current) along the long zone. An adjustable impeller changes the liquid level, which affects the pressure on the solids.

The solids 308 include cake like consistency and small amount of liquids or water. The solids 308 may include protein, zein, germ, insoluble fiber, insoluble starch, non-fermentable carbohydrates, inorganic acids (i.e., acetic acid, lactic acid, butyric acid), by-products, microorganisms, and dissolved solids. The solids 308 may comprise about 10% to about 40% total solids, which may include about 1% to about 5% dissolved solids and about 10% to about 40% suspended solids. The solids 308 may include about 2% to about 15% fat and about 20% to about 50% protein.

The liquids 310 include water, oil, microorganisms, protein, zein, germ, insoluble fiber, insoluble starch, non-fermentable carbohydrates, inorganic acids (i.e., acetic acid, lactic acid, butyric acid), by-products, and dissolved solids. The liquids 310 may comprise about 4% to about 12% total solids, which may include about 3% to about 7% dissolved solids and about 1% to about 5% suspended solids. The liquids 310 may include about 12% to about 36% fat.

Total solids refer to the components in the process stream that are not liquids. Dissolved solids (also referred to as solubles in water) refer to solid particles mixed with liquid in a process stream, which do not separate from the process stream during mechanical processing. Suspended solids (also referred to as insolubles) refer to suspended particles mixed with liquid in a process stream, which will separate from the process stream during mechanical processing. These terms are used to refer to, by weight.

The FSS process 300 will increase the concentration of the solids content in the process stream. As a result, the amount of natural gas and electricity used for evaporating and/or drying the insoluble solids downstream is greatly reduced, and the amount of GHG and/or carbon emissions from the evaporators and dryers are reduced as well.

In an embodiment, the FSS process 300 may further send the liquids 310 through a Single Cell Protein (SCP) process and/or send the process stream 302 through a SCP process. The SCP process is presented at a high level in a back end of the production facility. Details of embodiments of the SCP process will be discussed later with reference to FIGS. 13-15. The SCP process may be included with any process as part of the dry grind process or any type of process in a production facility. Specifically, the SCP process helps to produce valuable animal feed products.

Figure 4:
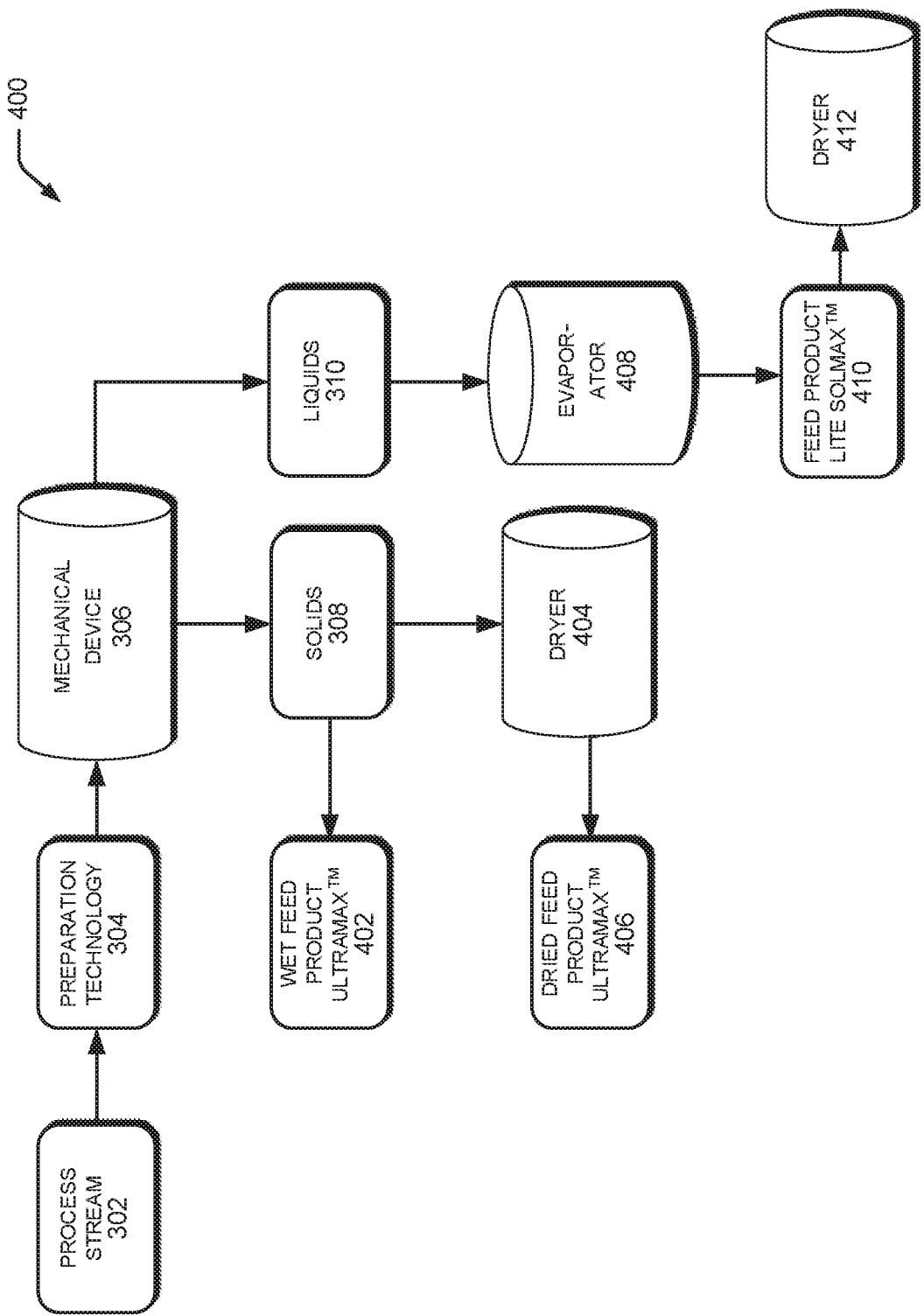

FIG. 4 is similar to FIG. 3, except this figure illustrates another embodiment of the FSS process. Details that are not similar to FIG. 3 will be discussed below with reference to FIG. 4. The mechanical device 306 separates the solids 308 from the liquids 310 based on density differential. The solids 308 may include protein, organic acids, non-fermentable carbohydrates, by-products, and the like. The solids 308 may be sold under a trademarked name for a wet feed product UltraMax™ 402. The wet feed product 402 may include compositions about 15% to about 40% total solids, protein ranging from about 20% to about 50%, and digestibility. The solids 308 may be further processed, being sent through a dryer 404 to create a product, under a trademarked name for the dried feed product UltraMax™ 406. The dried feed product UltraMax™ 406 may include compositions of a minimum dry matter of 90%, a minimum protein of 35%, and a maximum Neutral Detergent Fiber (NDF) of range 10% to 50%.

The dryer 404 may include, but is not limited to, a rotary drum dryer, a steam tube dryer, a scrape surface rotary contact dryer, a flash dryer, a ring dryer, a thin film steam dryer, a spray dryer, a compression dryer, a freeze dryer, a microwave, and the like. The dryer may be the same dryer as the dryer in FIG. 1 or another separate dryer.

Turning to the right side, the FSS process 400 sends the liquids 310 to evaporator 408 to evaporate a portion of the separated liquids 310 and generate a condensed stream 410. In an example, the condensed stream 410 can be used as a feed product 410, such as the feed product 410 having the trademark name Feed Product Lite SolMax™ 410. The evaporator may be the same evaporator as the evaporator in FIG. 1 or another separate evaporator. The Feed Product Lite SolMax™ 410 may contain glycerine, syrup, organic acids, by-products, non-fermentable carbohydrates, and the like. The Feed Product Lite SolMax™ 410 comprises a mixture of liquid materials having a range of about 55% total solids, a minimum dry matter of about 40% to about 70%, a minimum protein of greater than or equal to about 7% to about 27%, a minimum potassium of 0.5% to about 6%, and glycerin ranging from about 5% to about 30%. Lite Sol-Max™ 410 has about 1% to about 70% total solids, about 1% to about 40% dissolved solids, and about 0% to 30% suspended solids.

Next, the condensed stream 410, e.g., the feed product 410, can be sent to a dryer 412 to provide a dried feed product. The dryer may include, but is not limited to, a rotary drum dryer, a scrape surface rotary contact dryer, a steam tube dryer, a flash dryer, a ring dryer, a thin film dryer, a spray dryer, a compression dryer, a microwave, a freeze dryer, and the like. The dryer may the same dryer as in FIG. 1 or another dryer. In another embodiment, the FSS process 400 sends the process stream from the evaporator 408 through a SCP process.

Figure 5:
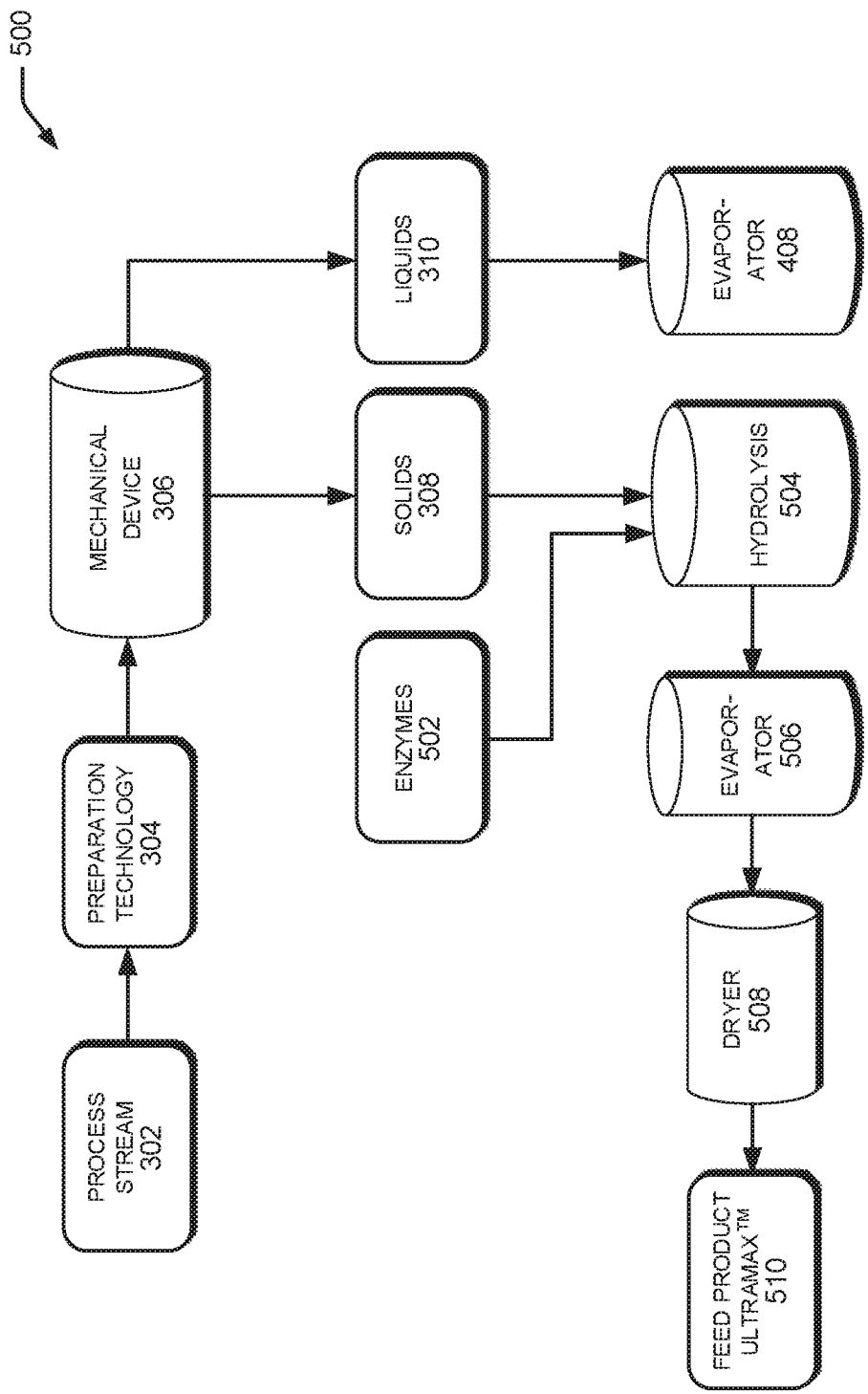

FIG. 5 is similar to FIG. 3, except this figure illustrates another embodiment of the FSS process. Details that are not similar to FIG. 3 will be discussed below with reference to FIG. 5. Here, the FSS process 500 adds enzymes 502 which are combined with the solids 308 to hydrolysis 504 or enzymatic hydrolysis. Hydrolysis 504 is a chemical breakdown of a compound due to reaction with water. The FSS process 500 sends the hydrolysate from hydrolysis 504 to evaporator 506, through a dryer 508 to create a feed product 510.

The addition of the enzymes may help reduce the viscosity by concentrating the process stream to a higher total solids. The enzymes may include, but are not limited to, beta-glucanase enzyme, protease enzyme, cellulase enzyme, hemicellulase enzyme, and the like. The enzymes may be added in an amount ranging from 0.01% to 0.5% weight of enzymes to dry weight of total solids, depending on the concentration of the enzymes or its substrate, activity of an enzyme, of active cells, and the like. Factors affecting the enzyme reactions include, but are not limited to, temperature, pH, enzyme concentration, substrate concentration, presence of inhibitors or activators, and the like.

The beta-glucanase enzyme breaks down beta-linked glucose polymers that are associated with grains. The β-1, 3 glucanase breaks down β-1, 3-glucans (1→3), a polysaccharide made of glucose sub-units. The β-glucan break down may occur randomly of the molecule. The β-1, 6 glucanase enzyme breaks down β-1, 6-glucans. Furthermore, there are beta-glucanse enzymes that break down β-1, 4-glucans. The amount of beta-glucanase added may range from 0.003% to 0.15 w/w % (depending on specific activity of enzyme formulations) of incoming grain and added at temperature ranges from about 20° C. to about 95° C. The beta-glucanase does not need a low temperature, so the risk of bacterial contamination is avoided.

Beta-glucanase has been found to be particularly effective with some larger chains, as it attacks (1→3), (1→4)—β-glucan fiber to liberate smaller fragments (i.e., a cell wall modification). The rate of modification is determined by contents of the cell walls of beta-glucan. Beta-glucanase hydrolyzes beta D-glucan component and breaks down the beta-linked glucose polymers that are often associated with cereal grains. Beta-glucanase has a high degree of stability that makes it durable to pH extremes. The pH of the hydrolysis may be adjusted from about 4.0 to about 6.5. The enzymes 502 may be processed in hydrolysis 504 for about 16 to about 32 hours.

The protease enzyme is known as an enzyme that performs proteolysis, a protein catabolism by hydrolysis of peptide bonds. The protein hydrolysis is the breakdown of protein into smaller peptides and free amino acids. The amount of protease enzyme added may range from 0.003% to 0.15% w/w % (depending on specific activity of enzyme formulations) of incoming grain and added at temperature ranges from about 20° C. to about 80° C. The pH of the hydrolysis may be adjusted from about 4.0 to about 6.5. The enzyme 502 may be processed in hydrolysis 504 for about 16 to about 32 hours.

Products were produced using the processes shown in FIGS. 4 and 5. A table for feed products 406, 510-A, and 510-B is shown in Table 1 below.

TABLE 1

| Nutrient Compositions and Digestibilities | | | |
|---|---|---|---|
| Nutrient | 406 | 510-A | 510-B |
| Crude protein, % AOAC Official Method 990.03 | 41.8 | 41.0 | 36.6 |
| TME, kcal/g$^a$ | 3.55 | 3.60 | 3.56 |
| NDF, % Ankom Method | 12.3 | 13.2 | 15.3 |
| ADF, % Ankom Method | 8.1 | 8.4 | 8.9 |
| Ether extract, % AOAC 945.16 | 8.3 | 8.0 | 7.7 |
| Calcium, % AOAC 985.01 (mod) | 0.07 | 0.08 | 0.08 |
| Phosphorus, % AOAC 985.01 (mod) | 1.02 | 0.93 | 1.01 |
| Potassium, % AOAC 985.01 (mod) | 1.02 | 0.95 | 1.00 |
| Sodium, % AOAC 985.01 (mod) | 0.23 | 0.23 | 0.25 |
| Sulfur, % AOAC 985.01 (mod) | 0.90 | 0.84 | 0.89 |
| Zinc, ppm AOAC 985.01 (mod) | 71.4 | 71.0 | 71.3 |
| Total glucan, % Megazyme MUSHROOM and YEAST BETA-GLUCAN ASSAY PROCEDURE K-YBGL | 17.4 | 18.4 | 19.4 |
| Alpha glucan Megazyme MUSHROOM and YEAST BETA-GLUCAN ASSAY PROCEDURE K-YBGL | 11.3 | 11.1 | 11.9 |
| Beta glucan Megazyme MUSHROOM and YEAST BETA-GLUCAN ASSAY PROCEDURE K-YBGL | 6.1 | 7.3 | 7.5 |
| Truly digestible amino acids, %$^b$ | 32.2 | 32.2 | 28.5 |
| Lysine | 1.37 | 1.06 | 1.41 |
| Methionine | 0.82 | 0.73 | 0.85 |
| Threonine | 1.47 | 1.29 | 1.51 |

$^a$Truly metabolizable energy (TME), measured using assays by Carl Parsons at University of Illinois.
$^b$measured using assays by Carl Parsons at University of Illinois.

This table illustrates the nutrient compositions as measured using standard analytical methods according to the Association of Official Analytical Chemists (AOAC), Ankom Technology, Megazyme, and Dr. Carl Parsons. AOAC INTERNATIONAL is the forum for finding appropriate science-based solutions through the development of microbiological and chemical standards. AOAC standards are used globally to promote trade and to facilitate public health and safety. The test methods that were used with their test method numbers are shown after each of the nutrients. Ankom Technology developed Filter Bag Technology (FBT) to provide a state of the art, low cost, high volume alternative system for determining conventional fiber analysis. The neutral detergent fiber (NDF) in the stillage protein products can be measured according to the Neutral Detergent Fiber in Feeds—Filter Bag Technique (for A200 and A2001), as developed and defined by Ankom Technology, and referred to as (NDF Method, Method 13, last revised on Sep. 21, 2016). The NDF is the residue remaining after digesting in a detergent solution. The fiber residues are predominantly hemicellulose, cellulose, and lignin. The acid detergent fiber (ADF) in the stillage protein products can be measured according to the Acid Detergent Fiber in Feeds-Filter Bag Technique (for A200 and A2001), as developed and defined by Ankom Technology, and referred to as (ADF Method, Method 12 last revised on Sep. 21, 2016). The ADF is the residue remaining after digesting with sulfuric acid and detergent solution. The fiber residues are predominantly cellulose and lignin.

Megazyme is a global leader in analytical reagents, enzymes and assay kits. β-Glucan (Yeast & Mushroom) Assay Kit (K-YGBL) is suitable for the measurement and analysis of 1,3:1,6-beta-glucan, 1,3-β-glucan and α-glucan in yeast, mushroom (fungi), algae and higher plants preparations. The truly metabolizable energy and truly amino acid digestibilities are measured using the procedures of Parsons et al., 1985. These test methods were used to measure the information that is shown in the other tables.

The feed products were made using the processes described in FIGS. 4 and 5. Product 510-A was dried with a scrape surface rotary dryer, while Product 510-B was dried with a spray dryer. Additional data is shown in the Examples Section.

Figure 6:
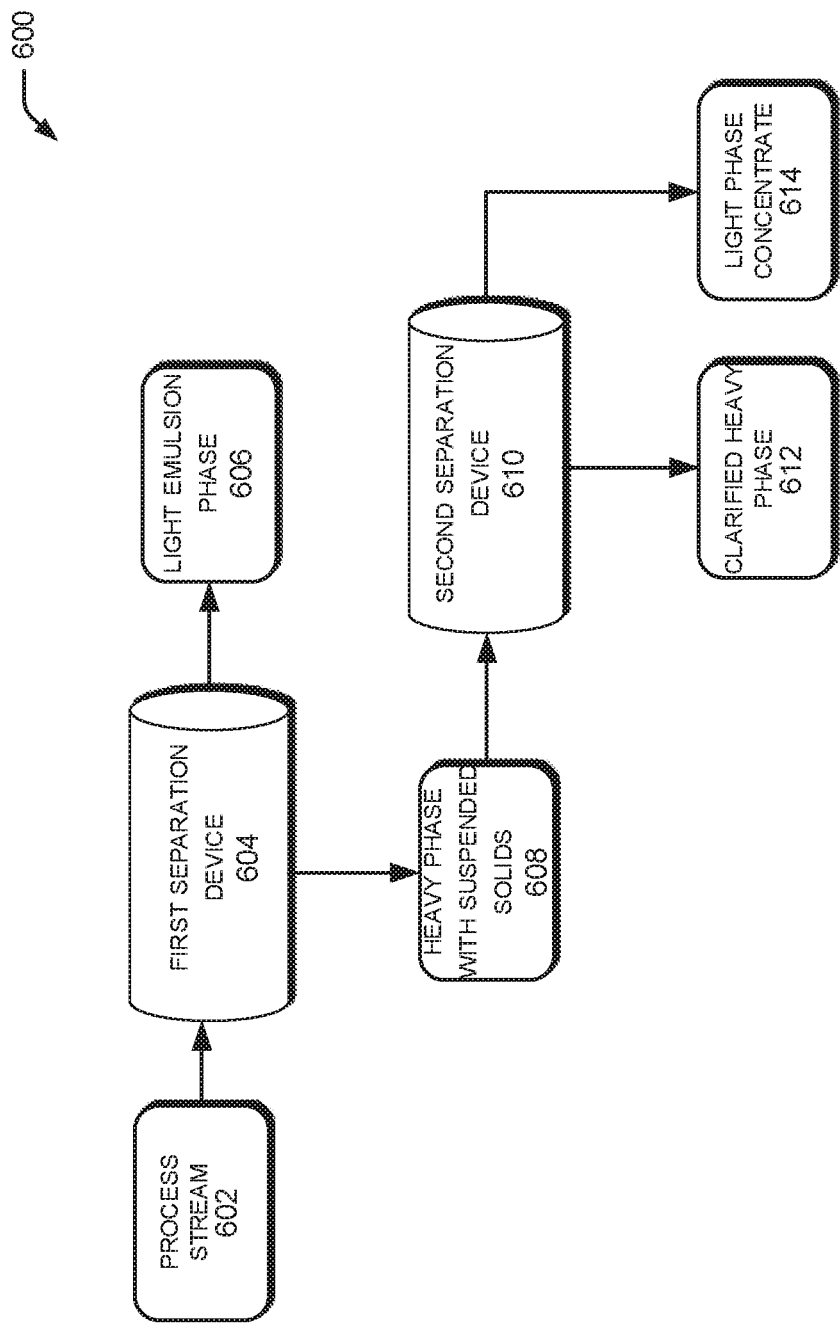
FIGS. 6-7 illustrate additional examples of FSS processes using a first separation device and a second separation device to separate components to create streams of different phases.

FIG. 6 illustrates another embodiment of the FSS process 600 with two separation devices. Any number of separation devices may be used, ranging from one, two, three, or more separation devices. The separation devices may be used in combination with the mechanical device 306. The separation devices recover valuable components such as oil, may be of suitable high purity and reduce the load on the equipment for further downstream processing. As a result, this helps increase oil availability, improve evaporator operation, increase dryer throughput, and reduce water consumption by recycling clean water to the front end, such as evaporator condensate.

The starting material shown as process stream 602 may be from fractionated stillage 132, may be from liquids 310 from the mechanical device 306, decanter centrate, backset, or from another process stream in a production facility. The process stream 602 may range from about 4% to about 14% total solids, about 3% to about 9% dissolved solids, and about 1% to about 5% suspended solids. Furthermore, this process stream 602 may contain about 12% to about 36% fat.

The FSS process 600 sends this process stream 602 through a first separation device 604 to create a light emulsion phase 606 and a heavy phase with suspended solids 608. The first separation device 604 may include, but is not limited to, a dissolved air floatation device, an open tank dissolved air floatation device, a dispersed air floatation device, an electrolysis flotation device, a settling tank, a hydrocyclone, and the like.

In an embodiment, the first separation device 604 may be an open tank for treating process streams that are heavily loaded with solids that need significant amounts of space for flotation and separation. The process stream 602 goes through in a flow-through manner to enter at one end of rectangular shape and to exit on the opposite end of the rectangular shape. The open tank may include a dewatering grid of rectangular array steel plates to hold the solids in place as it thickens. A skimmer can rotate with the flow of the process stream 602 in a co-current matter. The array steel plate skims the oil with the solids in the top layer, to remove a concentrated fat layer. An example of a model is an open tank PWL-Series 160W DAF Systems by FRC Systems International. Some specifications for a design model may include: flow rate may range from 640 to 1020 gpm, free area range from 320 to 500 sq ft, dry weight range from 20,000 to 26,200 lbs, wet weight range from 137,300 to 185,500 lbs. and a rectangular size range in size from 36 ft×11 ft×10 ft to 57 ft×11 ft×10 ft (L×W×H). Advantages of the rectangular array steel plates are to control thickness, eliminate pre-mature removal of solids, reduce build-up, and generate a drier product.

There may be a specialty pump associated with the separation device to draw air or receive inlet feed into a chamber or turbine shears the air to form bubbles for continuous operation. A recycle pump may be associated with the first separation device 604 to achieve a desired pressure.

Emulsion refers to a mixture of two or more immiscible (unblendable) liquids that are soluble within each other. Emulsions are part of a more general class of phase systems of matter called colloids. Although the terms colloid and emulsion are sometimes used interchangeably, emulsion tends to imply that both the dispersed and the continuous phase are liquid. In an emulsion, one liquid (the dispersed phase) is dispersed in the other (the continuous phase). The emulsion may be water-in-oil-over solid or oil-in-water over solid, depending on the volume fraction of all phases.

The emulsion may include, but is not limited to, components, such as oil, starches, free fatty acids (FFA) (e.g., arachidic acid, stearic acid, palmitic acid, erucic acid, oleic acid, arachidonic acid, linoleic acid and/or linolenic acid), fatty acid lower (alkyl) esters, phospholipids, grain germ fractions, yeast, protein, fiber, glycerol, residual sugars, other organic compounds and/or other inorganic compounds such as anion and cation salts of organic acids (e.g., metallic salts such as sodium sulfate, sodium sulfite, magnesium sulfate and potassium phytate, magnesium phytate, magnesium phosphate, sodium carbonate, magnesium oxalate, calcium oxalate, carotenoids, and/or antioxidants).

The first separation device 604 recovers oil and passes the suspended solids through for further processing to another separation device. The recovery rate for the first separation device 604 for total suspended solids range from about 4% to about 15%. The light emulsion phase 606 includes oil, water, protein, fiber, insolubles and the like. The light emulsion phase 606 comprises from about 7% to about 21% total solids, from about 3% to about 9% dissolved solids, and from about 4% to about 12% suspended solids. The light emulsion phase 606 further comprises from about 20% to about 60% fat, from about 8% to about 24% available oil and from about 7% to about 22% protein. The heavy phase with suspended solids 608 includes from about 4% to about 13% total solids, about 3% to about 9% dissolved solids, and about 1% to about 4% suspended solids. Furthermore, the heavy phase with suspended solids may contain about 11% to about 34% fat and from about 1% to about 3% available oil.

Next, the process 600 sends the heavy phase with suspended solids 608 through a second separation device 610 to create a clarified heavy phase 612 and a light phase concentrate 614. The second separation device 610 may include, but is not limited to, a dissolved air floatation device, an open tank dissolved air floatation device, a filter press, a DSM screen, a sieve bend screen, and the like.

In an embodiment, the second separation device 610 may be an open tank for treating process streams with recirculated water from the device, which may be super saturated with dissolved air. The heavy phase with suspended solids 608 combined with the water, cause bubbles to attach to solid particles, providing buoyancy to surface in the open tank. Solids will accumulate in the top layer, where a skimmer can push the solids toward a discharge hopper. Solids that do not float will sink to the bottom of the open tank, causing the settled solids to be concentrated. An example of a model is an open tank PCL-Series 180 DAF Systems by FRC Systems International. There may be a cross-flow plate pack design which gives surface velocity. Some of specifications for a design model may include: flow rate may range from 1320 to 1980 gpm, free area range from 108 to 151 sq ft, effective area from 2067 to 3100 sq ft. dry weight range from 16,000 to 23,500 lbs, wet weight range from 78,000 to 132,900 lbs, and dimensions range in size from 21 ft×8 ft×15 ft to 28 ft×8 ft×15 ft (L×W×H).

The second separation device 610 further processes the streams to create the clarified heavy phase 612 and the light phase concentrate 614. The recovery rate for the second separation device 612 for total suspended solids may range from about 60% to about 90%. The clarified heavy phase 612 comprises from about 3.2% to about 11% total solids, from about 3% to about 9% dissolved solids, and from about 0.2% to about 2% suspended solids. The clarified heavy phase 612 further comprises from about 1% to about 30% fat and from about 0.7% to about 20% available oil. A portion of the clarified heavy phase 612 may be sent to the first separation device 602 or the mechanical device 306, which would be composed of fat that would separate out based on density differences. This is all dependent on the corn seed quality, other parameters, mechanical actions, and the like.

The light phase concentrate 614 includes from about 10.5% to about 32% total solids, about 0.5% to about 2% dissolved solids, and about 10% to about 30% suspended solids. Furthermore, the light phase concentrate 614 may contain about 15% to about 65% fat, about 17% to about 50% available oil, and about 7% to about 21%/o protein. The recovery rate for total suspended solids based on the first separation device 604 and the second separation device 610 ranges from about 75% to about 98%, efficiency.

Figure 7:
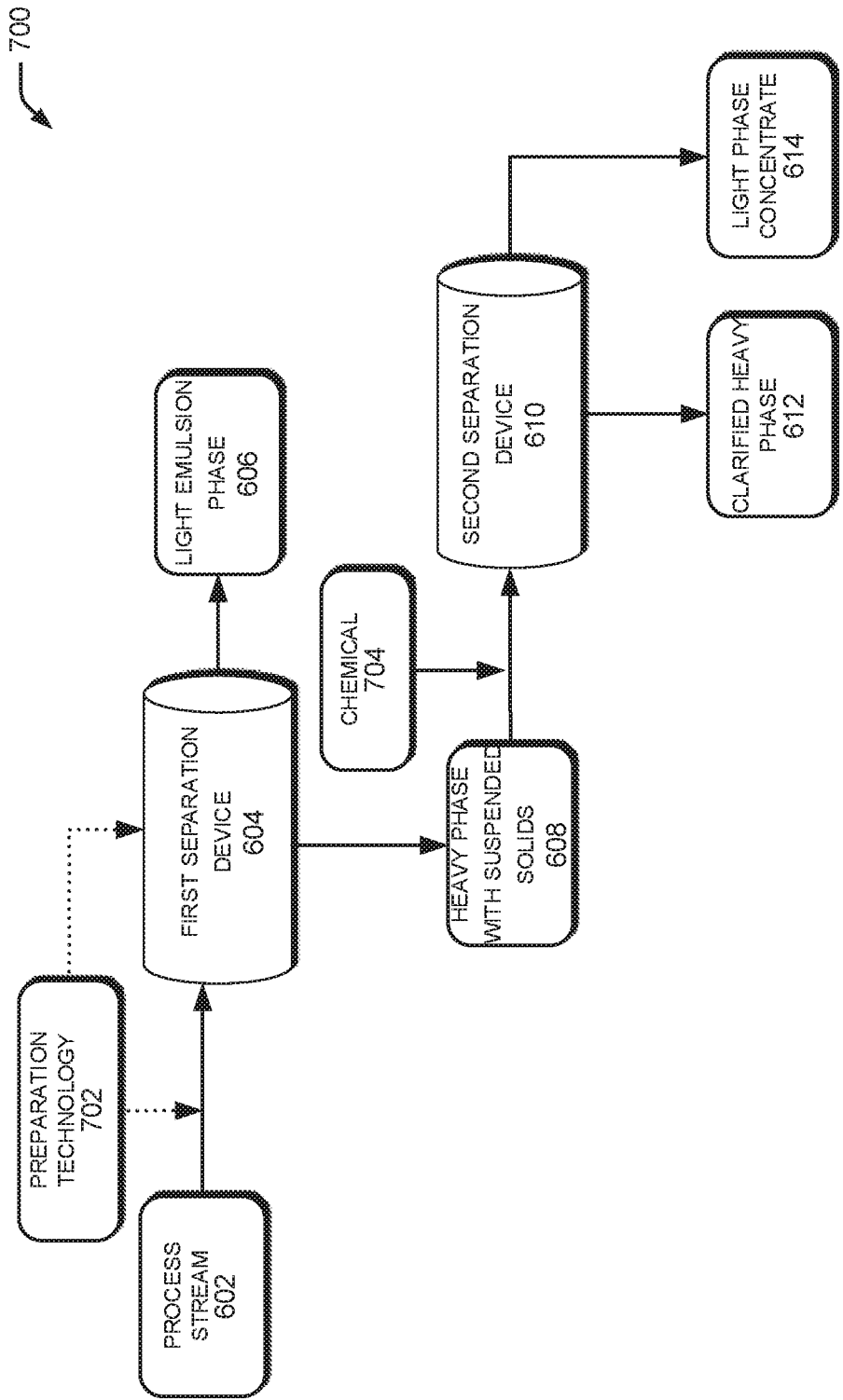

FIG. 7 is similar to FIG. 6, except this figure illustrates another embodiment of the FSS process. Details that are not similar to FIG. 6 will be discussed below with reference to FIG. 7. FIG. 7 illustrates another example of an FSS process 700 with a preparation technology 702 and a chemical 704. The preparation technology 702 may include air, nitrogen, carbon dioxide, other types of gases, and the like to generate bubbles under pressure. The preparation technology 702 may be applied online or in the first separation device 604. In an embodiment, the first separation device 604 may be a flotation device to separate solids from liquids by introducing the preparation technology 702, which may be fine gas bubbles to attach to the particulate matter. Particles or liquids less dense than water, such as oil, will naturally rise, while particles more dense than water can be made to rise by adding the preparation technology. The particles float to the surface, so skimming can occur based on the skimmer flights.

The chemical 704 may reduce the surface tension of water and may reduce the viscosity. The chemical 704 may include, but is not limited to, polymers, such as synthetic water-soluble polymers, dry polymers, emulsion polymers, inverse emulsion polymers, latex polymers, and dispersion polymers. The polymers may carry, a positive (i.e., cationic), a negative charge (i.e., anionic), or no charge (i.e., nonionic). Polymers with charges may include, but are not limited to, cationic flocculants, cationic coagulants, anionic coagulants, and anionic flocculants. The cationic (i.e., positive charge) and anionic (i.e., negative charge) polymers may have an ionic charge of about 10 to about 100 mole percent, more preferably about 40 to 80 mole percent. There are mineral flocculants that are colloidal substances, such as activated silica, colloidal clays, and metallic hydroxides with polymeric structure (i.e., alum, ferric hydroxide, and the like).

In embodiments, the chemical 704 may be based on a polyacrylamide and its derivatives or an acrylamide and its derivatives. An example is an active modified polyacrylamide. An example may include an acrylamide-acrylic acid resin C6H9NO3 (i.e., hydrolyzed polyacrylamide, prop-2-enamide; prop-2-enoic acid). The polymers have a specific average molecular weight (i.e., chain length) and a given molecular distribution. For instance, polyacrylamides have the highest molecular weight among synthetic chemicals, ranging from about 1 to about 20 million Daltons. There are other polymers with specific properties that may be used under specific conditions include, but are not limited to, polyethylene-imines, polyamides-amines, polyamines, polyethylene-oxide, and sulfonated compounds.

The chemical 704 may include, but is not limited to, surfactants, such as wetting agents, emulsifiers, foaming agents, dispersants, and the like. The surfactant contains a water insoluble (or oil soluble) component and a water soluble component. The surfactant may diffuse in water and adsorb at interfaces between air and water or at the interface between oil and water, in the case where water is mixed with oil.

The chemical 704 used is GRAS approved, meaning it satisfies the requirements for the United States' FDA category of compounds that are "Generally Recognized as Safe." Since the chemical 704 is GRAS approved, it does not need to be removed and may be included in the distillers grains and be fed to livestock and/or other animals when used within the dosage and application guidelines established for the particular product formulation. Also, the chemical 704 may be considered a processing aid under the government agencies, such as the U.S. Food and Drug Administration, the Center for Veterinary Medicine, and the Association of American Feed Control Officials based on their standards.

The process 700 adds an effective amount of the chemical 704 to the heavy phase with suspended solids 608 in an inline static mixer or in a tank. Other possible ways of adding the chemical 704 include, but are not limited to fed into a clarifier, a thickener feedwell, and the like. A dosage amount of the chemical 704 may range from about 10 to about 10,000 parts per million (ppm). Another dosage may be used in concentrations of about 0.05% to about 10% of chemical 704 according to standard practices for downstream applications. The chemical 704 may be added at varying concentrations, at different stages of the process, and the like. The dosage amount of chemical 704 depends on viscosity reduction desired, type of device used, and the like.

Figure 8:
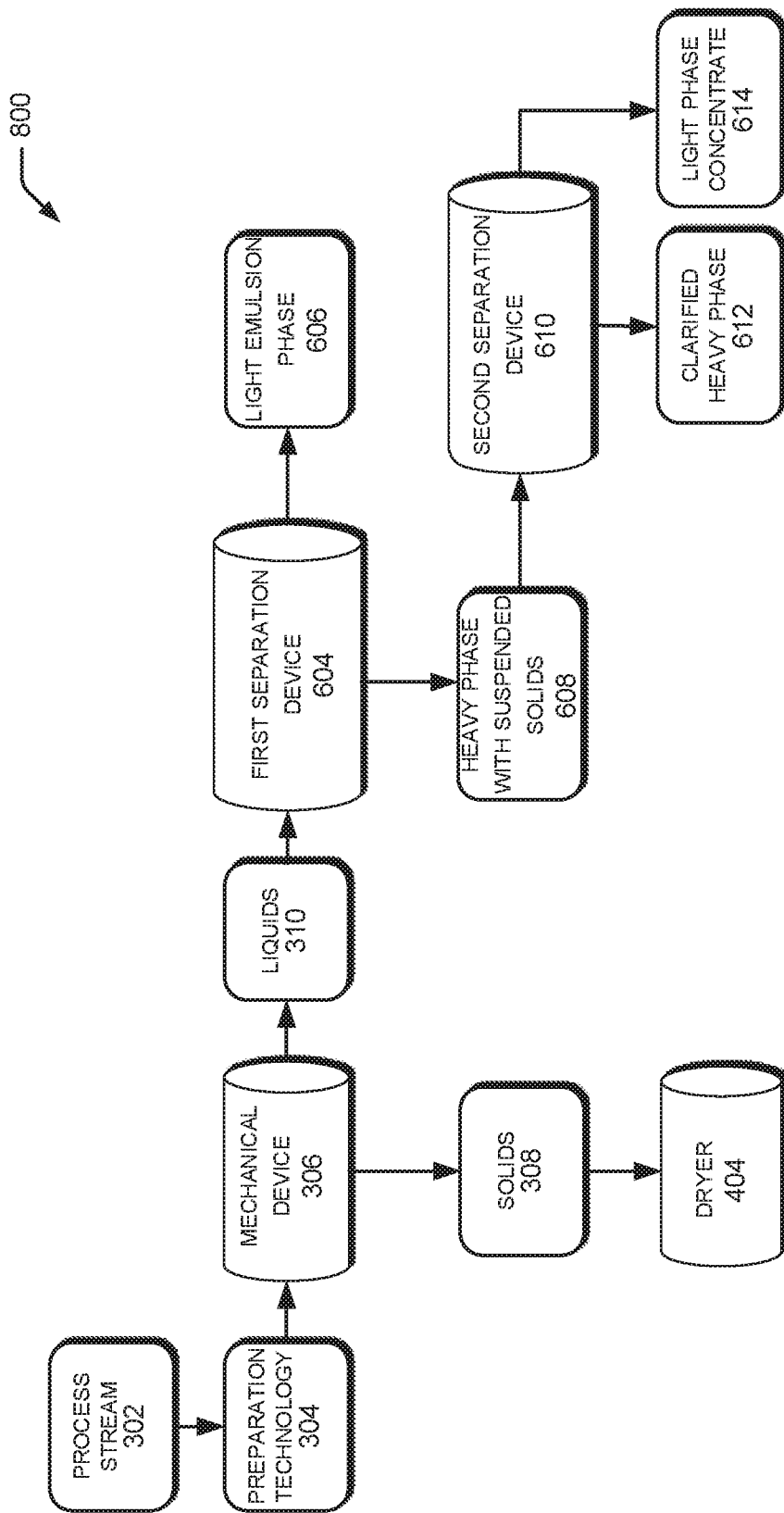
FIG. 8 illustrates an example of FSS process using a mechanical device, a first separation device and a second separation device to separate components to create streams of different phases.

FIG. 8 includes FIGS. 3 and 4, to illustrate the two processes may be combined into one process. This is a possible FSS process with three devices, as shown.

Figure 9:
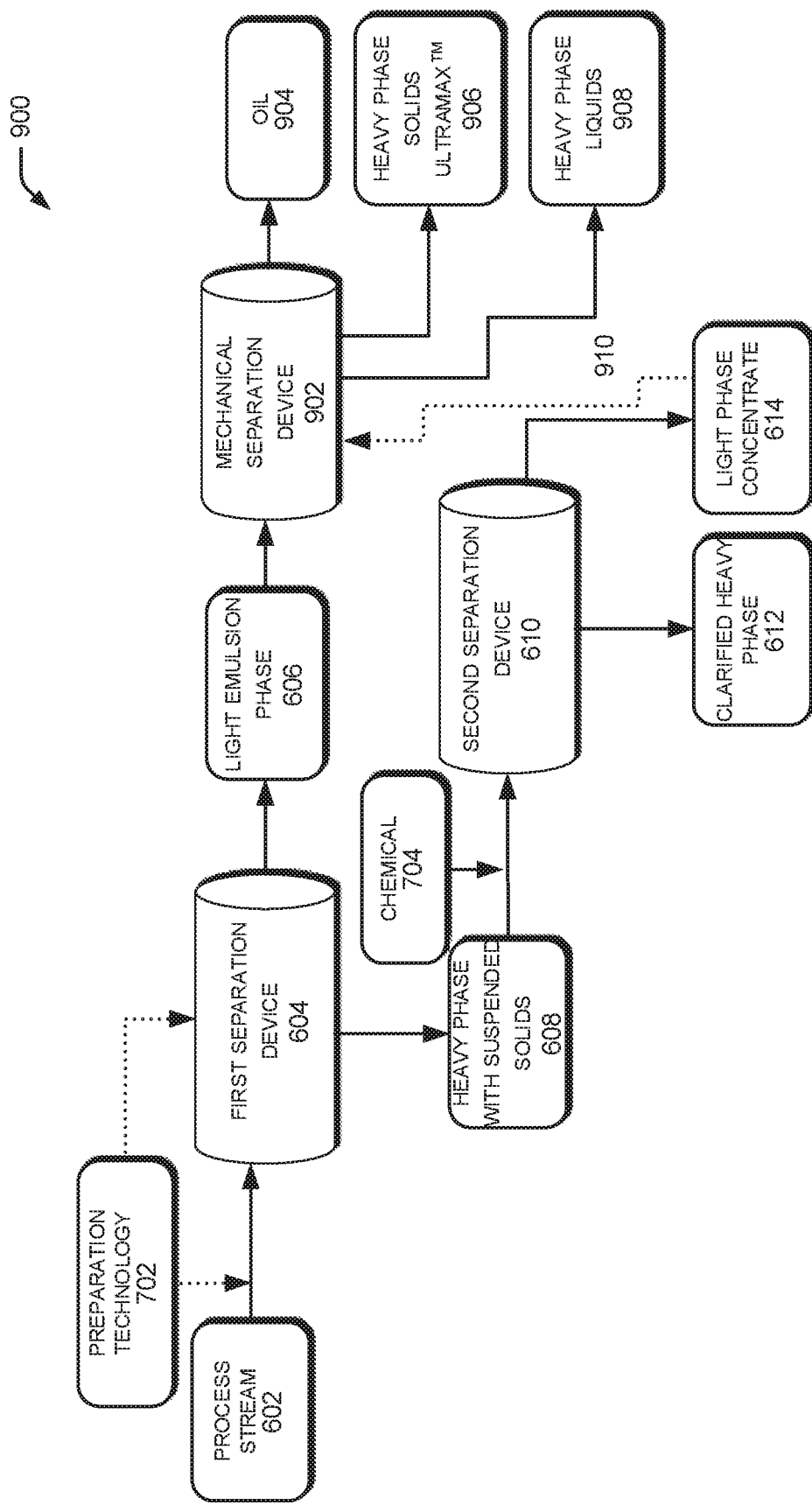
FIGS. 9-12 illustrate additional examples of FSS processes using a first separation device and a second separation device to separate components to create streams of different phases in combination with a mechanical separation device.

FIG. 9 is similar to FIG. 7, except this figure illustrates another embodiment of the FSS process. Details that are not similar to FIG. 7 will be discussed below with reference to FIG. 9. The FSS process 900 may send the light emulsion phase 606 through an oil recovery method using another type of mechanical device 902 to create one or more phases, such as oil 904, heavy phase solids UltraMax™ 906 (i.e., cake), and heavy phase liquids 908 (i.e., water with suspended solids). The mechanical device 902 may include, but is not limited to, a centrifuge, a tricanter centrifuge, a disk stack centrifuge, a hydrocyclone, and the like. The oil separation may be performed using methods described in U.S. Pat. No. 8,192,627, entitled Bio-Oil Recovery Methods, which is herein incorporated by reference in its entirety. Furthermore, the FSS process 900 may send a process stream, shown as a dotted line 910 from the light phase concentrate 614 to the mechanical device 902.

A portion 910 of the light phase concentrate 614 may be sent to mechanical separation device 902, suspended solids concentrate, or mechanical device 902. This portion may include fat.

Figure 10:
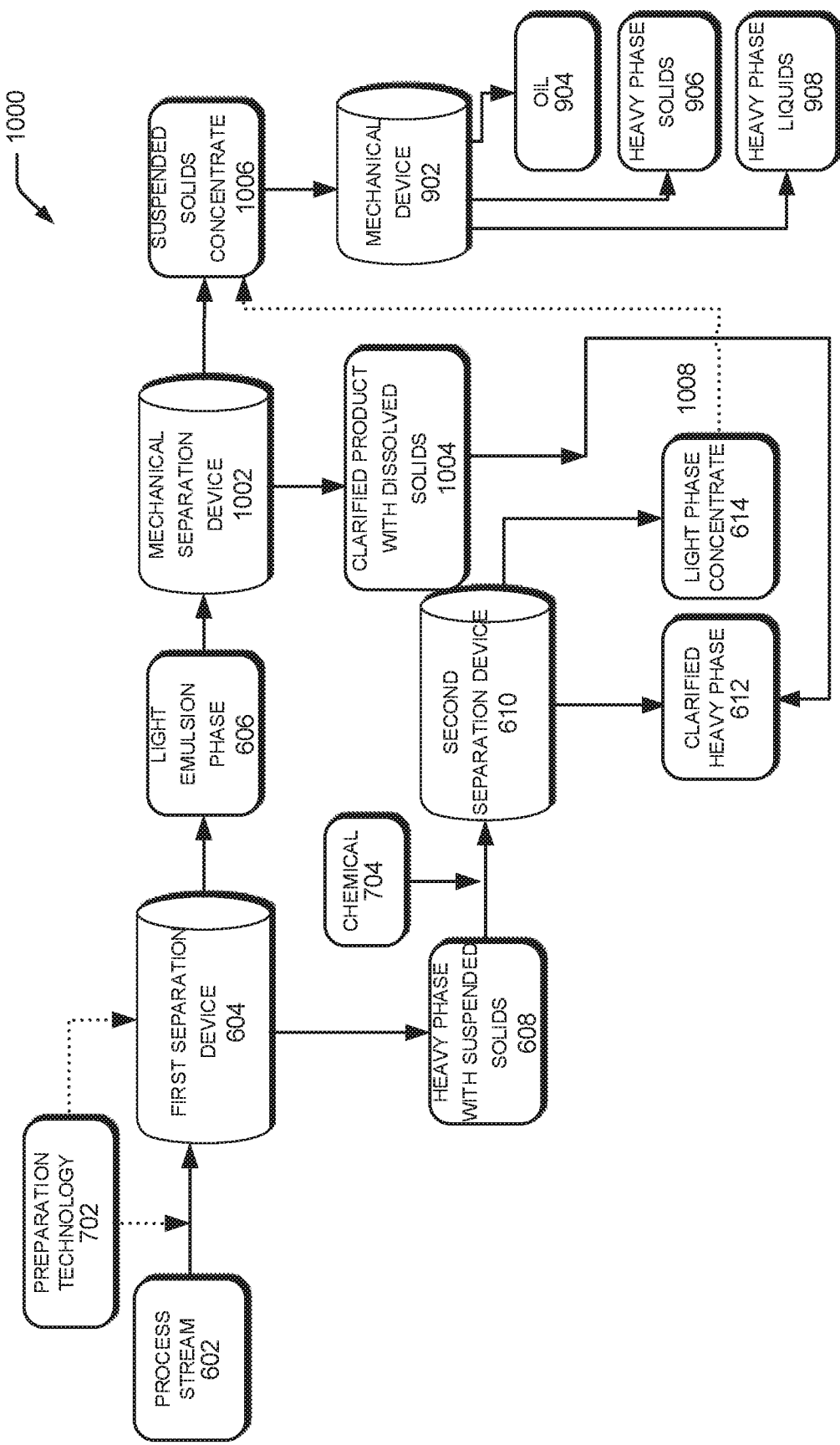

FIG. 10 is similar to FIG. 9, except this figure illustrates another embodiment of the FSS process. Details that are not similar to FIG. 9 will be discussed below with reference to FIG. 10. The FSS process 1000 sends the light emulsion phase 606 through a mechanical separation device 1002 to create clarified product with dissolved solids 1004 (also referred to as filtrate) and suspended solids concentrate 1006.

The mechanical separation device 902 may include, but is not limited to, ceramic, filtering centrifuge, vibratory shear-enhanced process, rotary drum vacuum filter, dynamic cross-flow filtration, cross-flow filtration, sand filter, deadend filtration, and the like. The experiments indicate temperature affected the filtration. The higher temperatures provided a product with less viscosity, which helped with filtration efficiency.

In an embodiment, the mechanical separation device 1002 may be a module, such as SmartFlow Technologies' OptiSep 11000 Series, which features an open channel design having multiple channels based on a patented ribbed configuration. Uniform flow is created by the combination of discrete retentate channels within the module and diagonally opposed inlet and outlet ports in the holder. This provides filter modules to offer improved fluid dynamics providing true linear scalability, optimized yields, decreased downstream process time, and reduced costs for an efficient separation. The module includes a broad range of membrane, channel height, membrane area, and processing parameters. Other factors may also include, but are not limited to, membrane pore sizes, different types of materials, and different types of solid polymer materials (i.e., face area).

A portion 1008 of the light phase concentrate 614 may be sent to mechanical separation device 902, suspended solids concentrate 1006, or mechanical device 902. This portion may include fat.

The clarified product with dissolved solids 1004 (also referred to as filtrate). The FSS process 1000 sends the clarified product with dissolved solids 1004 to the clarified heavy phase 612.

The suspended solids concentrate 1006. Next, the FSS process 1000 sends the suspended solids concentrate 1006 to the mechanical device 902 for oil recovery.

Figure 11:
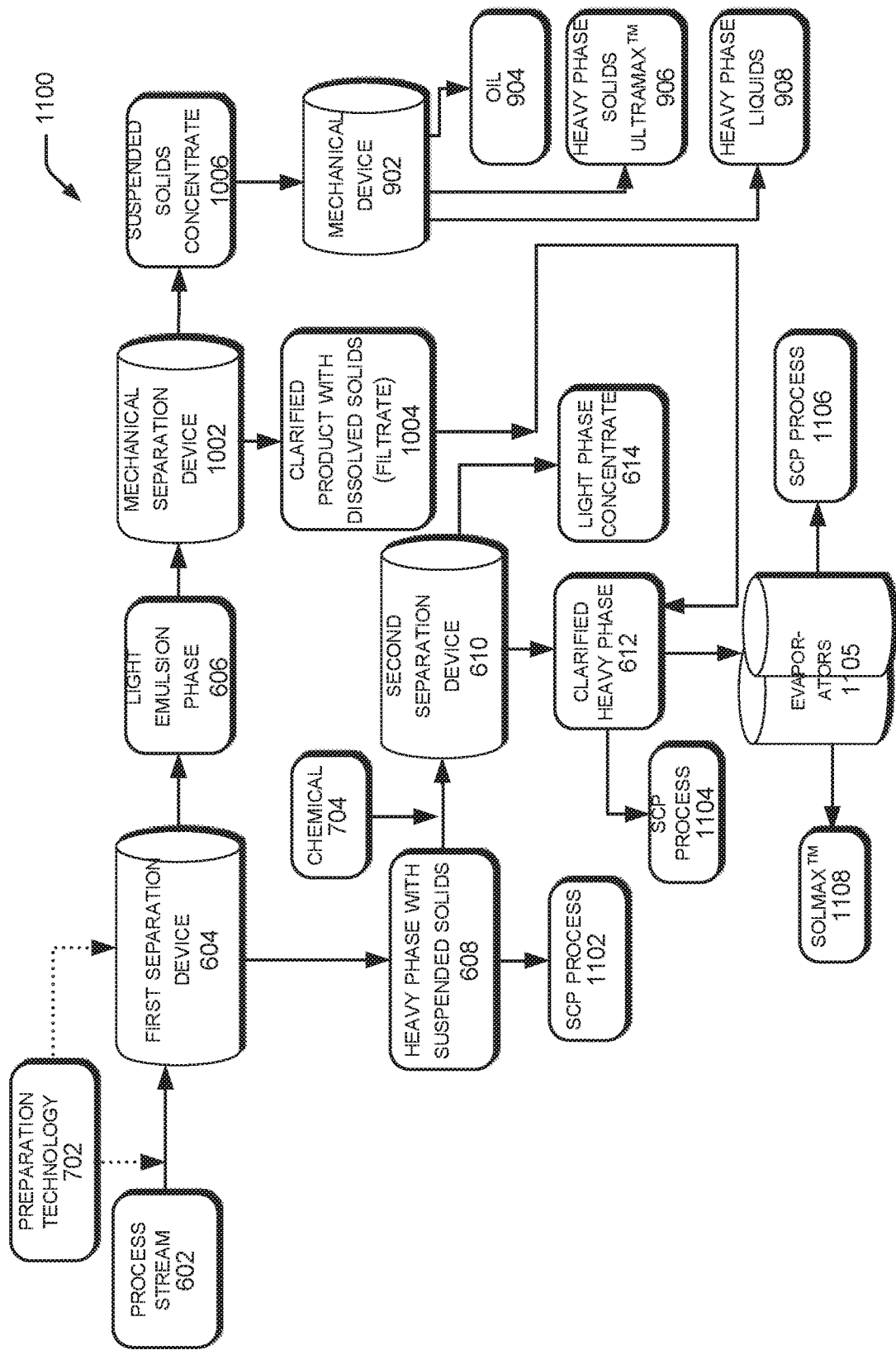

FIG. 11 is similar to FIG. 10, except this figure illustrates the SCP process with the FSS process. Details that are not similar to FIG. 10 will be discussed below with reference to FIG. 11. The SCP process cultivates SCP proteins that are useful in preparing animal feed products. The compositions of the SCP product may include high protein content ranging from about 30% to about 50% by weight, an amino acid profile that is high in lysine ranging from about 1% to about 9%, having more protein available for total digestible nutrients (TDN) (i.e., greater than 90% TDN), and good palatability. The FSS process 1100 may further send streams through the Single Cell Protein (SCP) process. The FSS process 1100 sends the heavy phase with suspended solids 608 though a SCP process 1102. In another embodiment, the FSS process 1100 sends the clarified heavy phase 612 through a SCP process 1104. The SCP process will be described in details with references to FIGS. 12-15. Also, the FSS process 1100 may send the clarified heavy phase 612 to evaporators 1105 and though a SCP process 1106. From the evaporator(s) 1105, the FSS process 1100 may create a trademark feed product, referred to as SolMax™ 1108.

In an embodiment, SolMax™ 1108 has liquid compositions of minimum dry matter about 40% to about 85%, a minimum protein of greater than or equal to about 10% to about 30%, a minimum potassium of about 2% to about 8%, and a minimum glycerin of about 20% to about 40%. In an embodiment, SolMax™ 1108 has about 1% to about 85% total solids, about 1% to about 55% dissolved solids, and about 0% to 30% suspended solids. The FSS process removes the suspended solids, while the dissolved solids increase in quantity.

Figure 12:
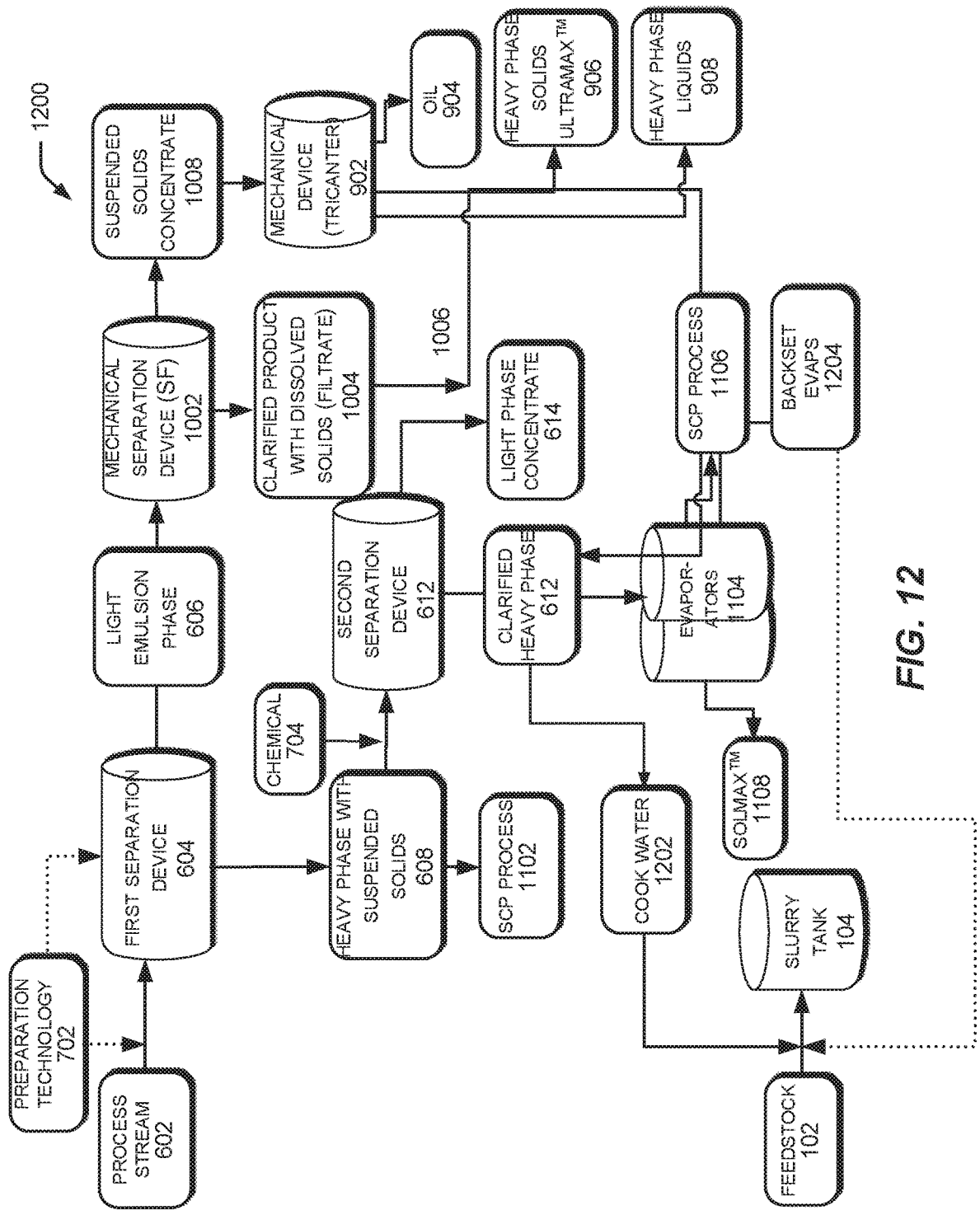

FIG. 12 is similar to FIG. 11, except this figure illustrates advantages from these processes. Details that are not similar to FIG. 11 will be discussed below with reference to FIG. 12. The process 1200 receives backset water 1202 from clarified heavy phase 612. This stream may be used as cook water where it is sent between feed stock 102 and slurry tank 104. Also, the process 1200 will send cook evaporate condensate 1204, which may include clean water, organic acids, syrup, and the like from evaporators 1104 to be used as cook water 1202 between feed stock 102 and slurry tank 104.

FIGS. 9-12 may be used without the preparation technology and/or may be used without the chemical. FIGS. 9-12 may be combined with the processes shown in FIGS. 3, 4, and 5. In the event that FIG. 3, 4 or 5 is combined, the liquids 310 would be used as the starting stream for process stream 602.

Examples of SCP Processes

Figure 13:
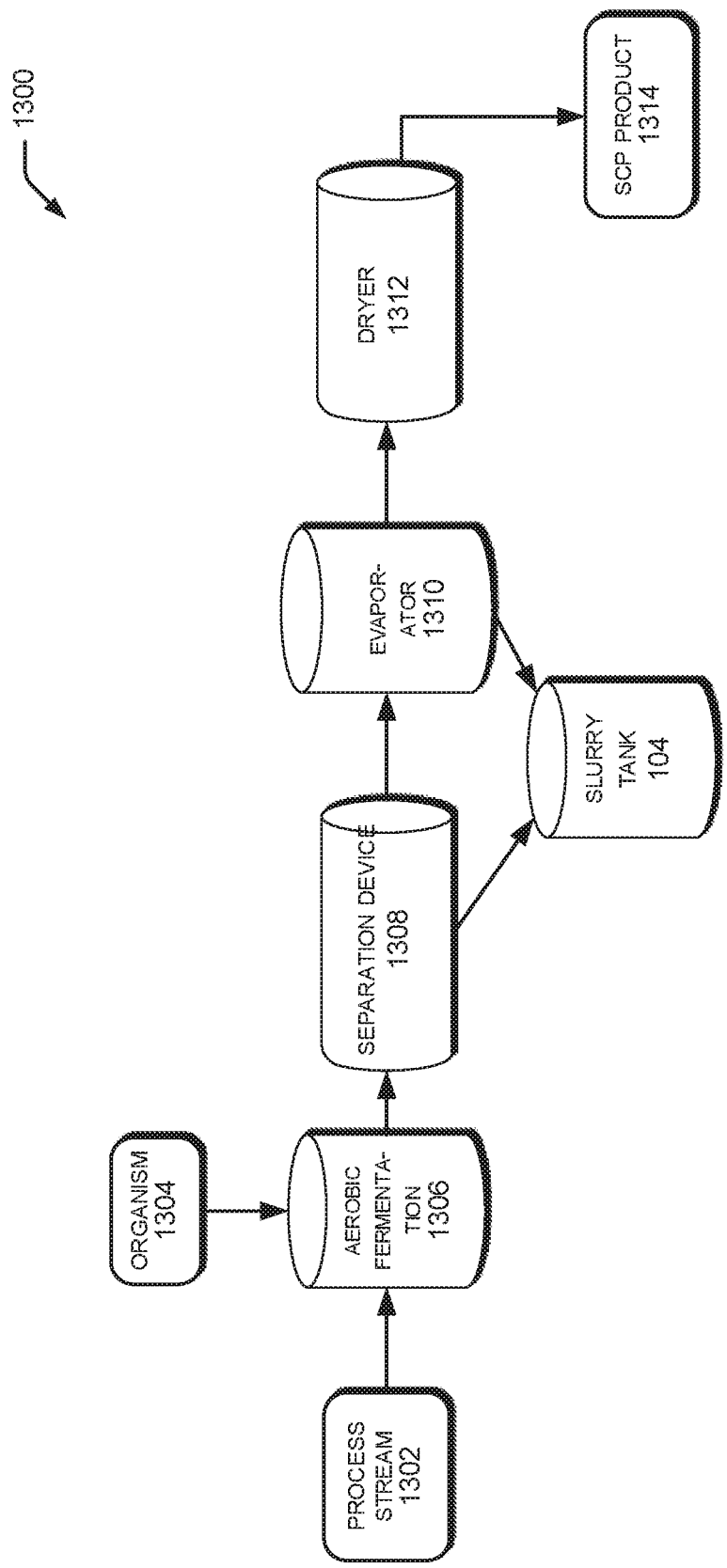
FIGS. 13-15 illustrate examples of single cell protein processes to create animal feed product.

FIG. 13 illustrates an embodiment of the SCP process with various types of equipment. There may be less or more equipment than shown and may be in any order. In an example, the SCP process 1300 receives a process stream 1302, which may be from heavy phase with suspended solids 608, from evaporators, fractionated stillage, liquids from the FSS process, streams after decanter, streams from evaporators (mid-stillage, thin stillage), and the like. The SCP process 1300 sends this stream to be combined with an organism 1304 to form a fermentation mixture. The organism 1304 that aerobically converts a carbon source that is in the process stream 1302 to a biomass, wherein the biomass is also referred to as a single cell protein. The biomass, e.g., the single cell protein, can form part of a feed product. The process 1300 performs aerobic fermentation 1306, which may be continuous or batch mode, runs from about 4 hours to about 48 hours. The SCP process 1300 sends the stream with the organism 1304 through a separation device 1308 to separate the liquids from the solids. The liquids from the separation device 1308 may be sent to the slurry tank 104. The separation device may be centrifuge. The SCP process 1300 sends the solids to the evaporator 1310, which then sends the solids to a dryer 1312 to create SCP product 1314, while recycling a stream of evaporator condensate to the slurry tank 104.

In an embodiment, the process 1300 may run about 4 hours to 6 hours for aerobic fermentation in continuous mode. The process 1300 will use a blower, compressor to provide air, oxygen, oxygen enrich air, or other gases to aerobic fermentation 1306. The temperature in the aerobic fermentation 1306 may be about 20° C. to about 40° C.

The organism 1304 should have ability to quickly convert organic material that is fed into a fermentor and have a high protein content. The organism 1304 may include, but is not limited to, *Candida utilis* (a.k.a. Torula yeast), *Saccharomyces cerevisiae, Pichia stiptis, Pichia pastoris. Escherichia coli. Kluyveromyces marxianus, Aspergillus oryzae, Corynobacterium lilim. Corynobacterium glutamicum*, and the like. The concentration of the organism placed in the aerobic tank may range from about 1% to about 30% by volume. This concentration varies depending on batch or continuous, process stream, organisms and the like.

The carbon source may include soluble proteins, carbohydrates, organic acids, alcohols, aldehydes, and fats. Examples of carbohydrates may include, but are not limited to, glycerol, mono and oligo-saccharides and combinations thereof. Examples of organic acids may include, but are not limited to acetic acid, lactic acid, succinic acid, and combinations thereof. Examples of fats may include but are not limited to, free fatty acids and other oil products.

Figure 14:
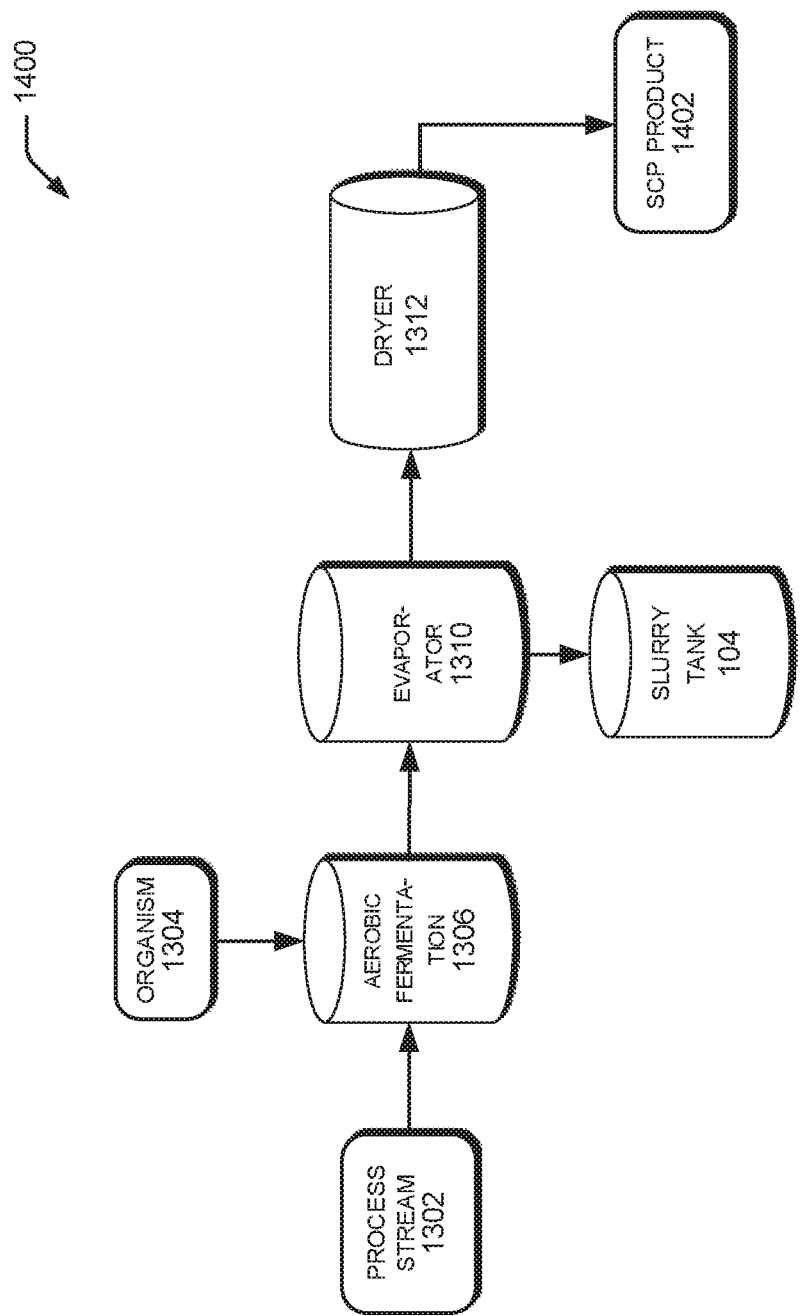

FIG. 14 is similar to FIG. 13, except this figure illustrates another embodiment of the SCP process. FIG. 14 does not include a separation process, but creates SCP Product 1402.

Figure 15:
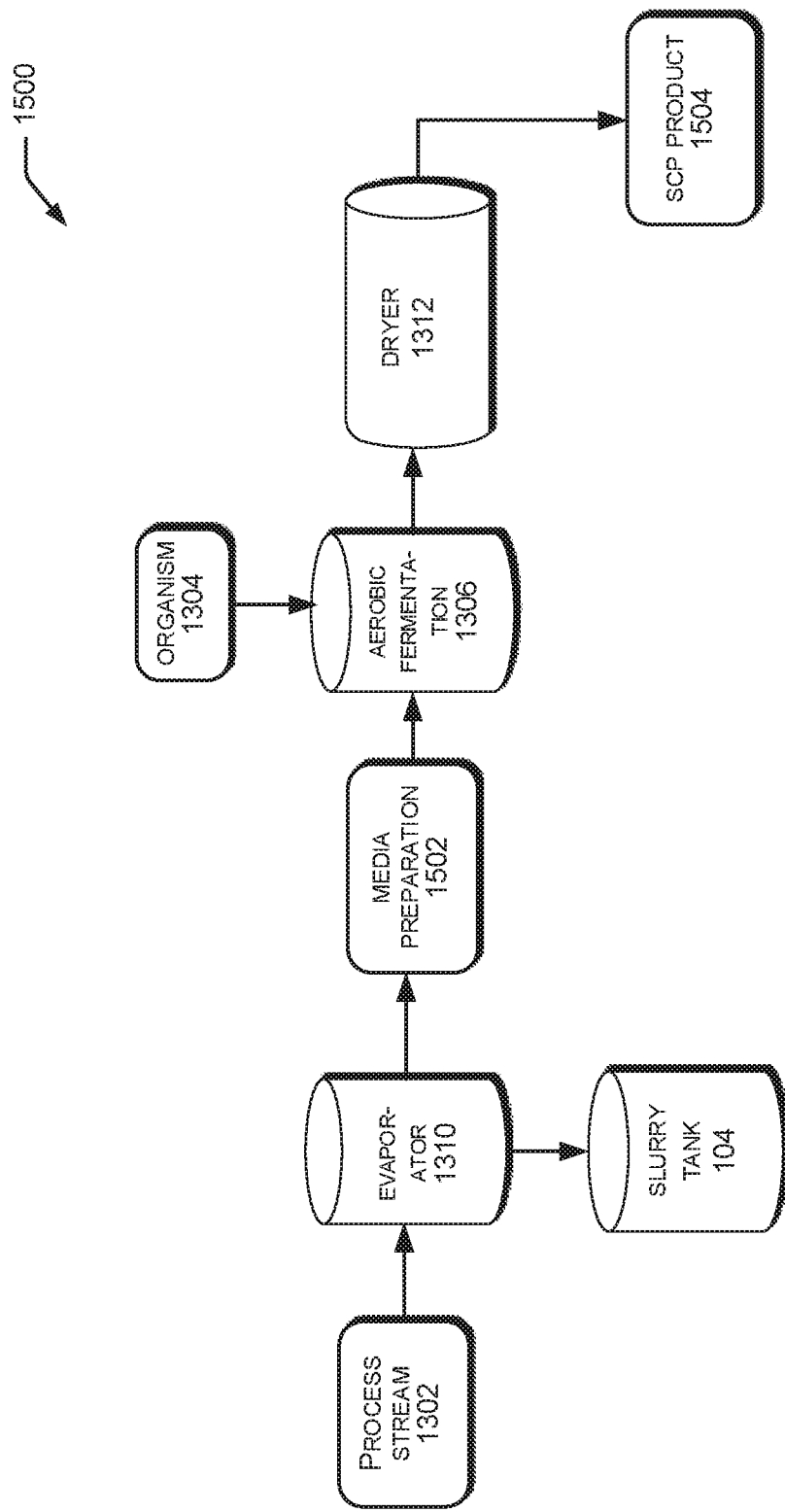

FIG. 15 is similar to FIGS. 13 and 14, except this figure illustrates another embodiment of the SCP process. Details that are not similar to FIGS. 13 and 14 will be discussed below with reference to FIG. 15. The SCP process 1500 shows a media preparation 1502, which is nitrogen sources, such as urea, ammonia, ammonia salts, a sterilizer, or a stream from the FSS process. The SCP process 1500 creates a SCP Product 1504.

Table 2 below illustrate composition data for the SCP Products.

TABLE 2

Composition Data for SCP Products

| Nutrient | SCP-1 | SCP-2 | SCP-3 |
|---|---|---|---|
| Crude protein, % | 42.9 | 39.3 | 46.8 |
| TME, kcal/g$^a$ | 1.54 | 2.67 | 2.17 |
| NDF, % | 11.7 | 19.6 | 12.7 |
| ADF, % | 1.8 | 3.7 | 8.1 |
| Ether extract, % | 1.0 | 5.5 | 6.4 |
| Calcium, % | 0.55 | 0.21 | 0.39 |
| Phosphorus, % | 2.54 | 2.52 | 1.55 |
| Potassium, % | 2.56 | 3.00 | 1.55 |
| Sodium, % | 0.74 | 0.79 | 0.56 |
| Sulfur, % | 0.65 | 1.26 | 0.89 |
| Zinc, ppm | 211.0 | 172.5 | 171.8 |
| Total glucan, % | 11.4 | 8.9 | 9.8 |
| Alpha glucan | 10.2 | 6.4 | 7.9 |
| Beta glucan | 1.2 | 2.5 | 1.9 |
| Truly digestible amino acids, %$^b$ | 14.5 | 13.9 | 15.6 |
| Lysine | 1.14 | 0.57 | 1.29 |
| Methionine | 0.23 | 0.23 | 0.21 |
| Threonine | 0.74 | 0.48 | 0.76 |

SCP-1 Products are produced using the processes described with reference to FIGS. 5 and 11. Specific SCP processes are described in details with reference to FIGS. 13-15. SCP-2 and SCP-3 Product is produced using the processes described with reference to FIGS. 13-15. The data show the truly digestible amino acids are present, such as lysine, methionine, and threonine.

Examples of Results

The FSS process was replicated in a pilot plant based on using a mixture of liquids and solids as the process stream. The temperature of the process stream was approximately 181 OF and pH was about 6.87.

TABLE I

FSS Process Data with Mechanical Device

| OPERATION | | Test No. | | | | | |
|---|---|---|---|---|---|---|---|
| DATA | | 1 | 2 | 3 | 4 | 5 | Avg. |
| Bowl speed | rpm | 3609 | 3609 | 3609 | 3608 | 3607 | 3607 |
| g-force | | 4848 | 4848 | 4848 | 4845 | 4843 | 4843 |
| Flow rate | GPM | 97-99 | 100.00 | 125.00 | 134.00 | 134.00 | 135 w air |
| Solids Recovery | % v/v | 90.0% | 90.0% | 92.0% | 92.0% | 91.7% | 94.4% |

Table I. indicates the data collected in the pilot plant runs. Table I shows in the first horizontal row of different runs, numbered as 1-5 Avg., and shows operation data, such as shown in the first column Bowl speed (rpm) g-force, flow rate (GPM), and Solids Recovery (% v/v). The data illustrates an average bowl speed used is about 3607 rpm, 4843 g-force, 135 gpm flow rate, and succeeded in 94.4% solids recovery rate.

Another set of experiments were conducted on the equipment in the pilot plant runs.

TABLE II

FSS Process Data with Mechanical Device

| OPERATION | | Test No. | | | | |
|---|---|---|---|---|---|---|
| DATA | | 6 | 7 | 8 | 9 | 10 |
| Bowl speed | rpm. | 3607 | 3607 | 3606 | 3606 | 3607 |
| g-force | | 4843 | 4843 | 4840 | 4840 | 4843 |
| Flow rate | GPM | 132.50 | 142.50 | 142.50 | 142.50 | 142.50 |
| Solids Recovery | % v/v | 91.3% | 92.5% | 92.5% | 93.8% | 93.8% |

Table II, illustrates an average bowl speed used is about 3607 rpm, 4843 g-force, 142 gpm flow rate, and succeeded in 93.8% solids recovery rate.

The UltraMax™ feed products were produced and tested in digestibility study. Table III. Shows the data as feed to roosters.

TABLE III

UltraMax ™ to Rooster

| | Thin Stillage Solids % Comp | Rooster Digestibility Coef. |
|---|---|---|
| Lysine | 2.02 | 92.4 |
| Methionine | 0.83 | 92.9 |
| TSAA | 1.53 | 90.0 |
| Threonine | 1.57 | 92.2 |
| Tryptophan | 0.37 | 94.0 |
| Valine | 2.30 | 92.6 |
| Arginine | 2.29 | 96.5 |
| Isoleucine | 1.70 | 91.0 |
| Crude Protein | 41.4 | N/A |

TSAA may be referred to as alkyl hydroperoxide reducatase. The feed products, 460, 510-A, and 510-B were produced in the pilot plant. Amino acid concentrations are shown below in Table IV.

TABLE IV

Amino Acid Concentrations (%)
AOAC Official Method 982.30

| | 406 | 510-A | 510-B |
|---|---|---|---|
| Amino Acid | 2.66 | 3.02 | 3.11 |
| Asparagine | 1.46 | 1.66 | 1.73 |
| Threonine | 1.53 | 1.71 | 1.82 |

TABLE IV-continued

Amino Acid Concentrations (%)
AOAC Official Method 982.30

|  | 406 | 510-A | 510-B |
|---|---|---|---|
| Serine | 4.70 | 5.18 | 5.38 |
| Glutamine | 2.48 | 2.65 | 2.76 |
| Proline | 1.61 | 1.78 | 1.86 |
| Glycine | 2.35 | 2.67 | 2.76 |
| Alanine | 0.71 | 0.79 | 0.82 |
| Cysteine | 2.11 | 2.41 | 2.50 |
| Valine | 0.79 | 0.88 | 0.90 |
| Methionine | 1.67 | 1.85 | 1.91 |
| Isoleucine | 3.75 | 4.23 | 4.40 |
| Leucine | 1.46 | 1.53 | 1.61 |
| Tyrosine | 1.83 | 1.94 | 2.01 |
| Phenylalanine | 1.40 | 1.62 | 1.75 |
| Lysine | 0.98 | 1.07 | 1.14 |
| Histidine | 1.95 | 2.15 | 2.29 |
| Arginine | 0.39 | 0.40 | 0.42 |
| Tryptophan | 2.66 | 3.02 | 3.11 |

The amino acid digestibilities for 406, 510-A, 510-B are shown in Table V. below. AOAC test method 982.30 was used as the standard test method for these amino acid concentrations.

TABLE V

Amino Acid Digestibilities (%)

|  | 406 | 510-A | 510-B |
|---|---|---|---|
| Amino Acid | 76.96 | 74.87 | 82.38 |
| Asparagine | 79.53 | 77.87 | 85.99 |
| Threonine | 85.22 | 81.67 | 89.43 |
| Serine | 85.97 | 83.05 | 89.54 |
| Glutamine | 85.26 | 83.35 | 90.83 |
| Proline | 85.69 | 83.25 | 89.12 |
| Glycine | 74.35 | 72.80 | 80.99 |
| Alanine | 82.51 | 79.51 | 86.77 |
| Cysteine | 89.33 | 83.20 | 92.48 |
| Valine | 84.04 | 81.25 | 86.55 |
| Methionine | 90.48 | 87.51 | 91.88 |
| Isoleucine | 86.51 | 84.28 | 89.41 |
| Leucine | 88.28 | 84.34 | 89.71 |
| Tyrosine | 61.12 | 65.70 | 78.36 |
| Phenylalanine | 83.15 | 82.08 | 89.23 |
| Lysine | 90.35 | 86.45 | 93.05 |
| Histidine | 86.37 | 85.62 | 85.81 |
| Arginine | 76.96 | 74.87 | 82.38 |
| Tryptophan | 79.53 | 77.87 | 85.99 |

In pilot plant experiments, the sedicanter centrifuge was evaluated for different parameters of scroll speed, impeller, pressure, bowl speed, torque, feed rate, and non-condensable media. Data for inorganic content were analyzed and shown to be consistent with the data table previously shown for feed products. Next, the media for SCP process was sterilized with steam from about 220° F. to about 280° F. for approximately one hour. The aerobic fermentation took about 34 to 38 hours, where the final yeasts count was about 1.58×108 CFU/ml. Table VI. shows mass composition data for the SCP product.

TABLE VI

Mass Composition for SCP

|  | min | max | SCP |
|---|---|---|---|
| Fat-Ankom_Fat Dry Basis AOCS Am 5-04 | 0.46 | 24.61 | 0.99 |
| LECO_Ave % Protein Dry Basis AOAC 990.03 | 37.78 | 46.80 | 43.75 |

TABLE VI-continued

Mass Composition for SCP

|  | min | max | SCP |
|---|---|---|---|
| Acid Detergent Fiber %_% ADF (Dry Basis) Ankom Technology Method-ADF | 11.75 | 19.27 | 11.75 |
| Crude Fiber %_% Crude Fiber (Dry Basis) AOCS Ba 6a-05 | 0.04 | 1.81 | 0.18 |
| Neutral Detergent Fiber %_% NDF (Dry Basis) Ankom Technology Method aNDF | 1.37 | 34.32 | 1.75 |
| Amino Acid Comp-Met & Cys (% Dry Weight)_Methionine AOAC Official Method 994.12, 985.28 | 0.38 | 0.45 | 0.46 |
| Amino Acid Comp-Met & Cys (% Dry Weight)_Cysteine AOAC Official Method 994.12, 985.28 | 0.46 | 0.64 | 0.60 |
| Amino Acid Comp-Tryptohpan (% Dry Weight)_Tryptophan AOAC Official Method 988.15 | 0.17 | 0.39 | 0.36 |
| Amino Acid Comp (% Dry Weight)_Aspartic Acid AOAC Official Method 994.12 | 2.65 | 3.64 | 3.54 |
| Amino Acid Comp (% Dry Weight)_Threonine | 1.57 | 2.14 | 1.90 |
| Amino Acid Comp (% Dry Weight)_Serine | 1.60 | 1.96 | 1.80 |
| Amino Acid Comp (% Dry Weight)_Glutamic Acid | 3.91 | 5.69 | 4.84 |
| Amino Acid Comp (% Dry Weight)_Glycine | 1.35 | 1.76 | 1.55 |
| Amino Acid Comp (% Dry Weight)_Alanine | 1.68 | 2.45 | 2.33 |
| Amino Acid Comp (% Dry Weight)_Valine | 1.38 | 1.63 | 1.63 |
| Amino Acid Comp (% Dry Weight)_Isoleucine | 1.15 | 1.38 | 1.33 |
| Amino Acid Comp (% Dry Weight)_Leucine | 2.01 | 2.67 | 2.25 |
| Amino Acid Comp (% Dry Weight)_Tyrosine | 0.79 | 1.13 | 1.08 |
| Amino Acid Comp (% Dry Weight)_Phenylalanine | 1.17 | 1.43 | 1.29 |
| Amino Acid Comp (% Dry Weight)_Lysine | 1.50 | 2.54 | 2.44 |
| Amino Acid Comp (% Dry Weight)_Ammonia | 0.53 | 0.96 | 0.69 |
| Amino Acid Comp (% Dry Weight)_Histidine | 0.71 | 0.92 | 0.90 |
| Amino Acid Comp (% Dry Weight)_Arginine | 0.95 | 1.71 | 1.20 |
| Amino Acid Comp (% Dry Weight)_Proline | 1.40 | 2.46 | 1.97 |

AOCS bring the world of fats and oils a little closer to home. Offered in several different formats, the Official Methods and Recommended Practices of the AOCS is essential for a lab testing edible fats and oils and similar compounds. The neutral detergent fiber (NDF) in the stillage protein products can be measured according to the Neutral Detergent Fiber in Feeds—Filter Bag Technique (for A200 and A2001), as developed and defined by Ankom Technology, and referred to as (NDF Method, Method 13, last revised on Sep. 21, 2016). The NDF is the residue remaining after digesting in a detergent solution. The fiber residues are predominantly hemicellulose, cellulose, and lignin. The acid detergent fiber (ADF) in the stillage protein products can be measured according to the Acid Detergent Fiber in Feeds—Filter Bag Technique (for A200 and A2001), as developed and defined by Ankom Technology, and referred to as (ADF Method. Method 12 last revised on Sep. 21, 2016). The ADF is the residue remaining after digesting with sulfuric acid and detergent solution. The fiber residues are predominantly cellulose and lignin.

AOAC Official Method 994.12 is the standard test method used to test the rest of the amino acid from threonine to proline. As shown by the data, these processes can create higher value feed product, of high quality that is superior to materials that have not been treated through these processes.

By HPLC 69.2 g/l of material were consumed, which created the 21.6 g/l increase of cell biomass, or a 0.312 g/g yield on carbon source. Most yeast produce biomass at a 0.45 g/g maximum, the run was at 69.36%. Other data show 3.5 gram, conversion rate 38% and oxygen 50 to 200 millimole per hour. Next, centrifuge separation of the batch produced nearly 1500 lbs of dried material. The aerobic fermentation temperature was from about 16° C. to about 48° C. A combination mix of beta-glucanase and protease happened at time 0 of the hydrolysis step, no pH adjustment was necessary with a starting pH of 5.37. The temperature was held constant at 120° F. and allowed 16 hours to hydrolyze. The enzyme treatment succeeded in breaking open cell walls and releasing more soluble components. The most drastic release was glucose, increasing to almost 14 g/l.

Feed products created using the SCP process were generated in the pilot plant. The amino acid compositions are shown in Table VII below.

TABLE VII

Amino Acid Concentrations (%)

| Amino Acid | SCP-A | SCP-B | SCP-C | SCP-1 | SCP-2 | SCP-3 |
|---|---|---|---|---|---|---|
| Asparagine | 2.93 | 3.11 | 3.03 | 3.01 | 2.63 | 3.15 |
| Threonine | 1.81 | 1.89 | 1.70 | 1.84 | 1.45 | 1.84 |
| Serine | 1.33 | 1.41 | 1.44 | 1.36 | 1.28 | 1.58 |
| Glutamine | 4.08 | 4.09 | 5.14 | 4.10 | 5.08 | 5.45 |
| Proline | 1.60 | 1.58 | 2.05 | 1.58 | 1.88 | 2.24 |
| Glycine | 1.64 | 1.65 | 1.79 | 1.64 | 1.78 | 1.91 |
| Alanine | 1.84 | 1.85 | 2.53 | 1.84 | 2.29 | 2.56 |
| Cysteine | 0.44 | 0.46 | 0.50 | 0.46 | 0.52 | 0.56 |
| Valine | 1.95 | 1.99 | 2.16 | 1.95 | 1.94 | 2.53 |
| Methionine | 0.45 | 0.48 | 0.56 | 0.46 | 0.49 | 0.69 |
| Isoleucine | 1.74 | 1.77 | 1.78 | 1.73 | 1.49 | 2.02 |
| Leucine | 2.32 | 2.38 | 2.82 | 2.33 | 2.59 | 3.61 |
| Tyrosine | 1.16 | 0.93 | 1.28 | 1.14 | 1.10 | 1.49 |
| Phenylalanine | 1.40 | 1.44 | 1.56 | 1.40 | 1.37 | 1.89 |
| Lysine | 2.29 | 2.41 | 2.26 | 2.28 | 1.72 | 2.12 |
| Histidine | 0.82 | 0.83 | 0.88 | 0.82 | 0.89 | 0.99 |
| Arginine | 1.15 | 1.30 | 1.68 | 1.18 | 1.40 | 1.68 |
| Tryptophan | 0.26 | 0.25 | 0.27 | 0.24 | 0.19 | 0.25 |

The amino acid digestibilities (%) are shown in Table VIII below.

TABLE VIII

Amino Acid Digestibilities (%)

| Amino Acid | SCP-A | SCP-B | SCP-C | SCP-1 | SCP-2 | SCP-3 |
|---|---|---|---|---|---|---|
| Asparagine | 50.66 | 39.36 | 45.34 | 48.62 | 36.52 | 41.94 |
| Threonine | 41.86 | 29.95 | 40.20 | 40.52 | 33.14 | 39.67 |
| Serine | 46.39 | 29.40 | 41.75 | 45.92 | 33.13 | 39.16 |
| Glutamine | 54.71 | 42.29 | 58.31 | 52.84 | 48.50 | 50.74 |
| Proline | 53.08 | 41.61 | 59.66 | 53.16 | 48.01 | 53.54 |
| Glycine | 53.09 | 40.38 | 58.00 | 50.68 | 49.46 | 51.66 |
| Alanine | 27.69 | 16.85 | 35.24 | 32.11 | 17.13 | 24.66 |
| Cysteine | 49.33 | 34.22 | 42.84 | 45.86 | 34.68 | 44.08 |
| Valine | 43.56 | 32.14 | 48.78 | 37.29 | 38.26 | 45.06 |
| Methionine | 53.63 | 41.02 | 47.52 | 49.93 | 40.78 | 49.33 |
| Isoleucine | 54.13 | 39.99 | 49.62 | 51.47 | 43.65 | 52.99 |
| Leucine | 52.70 | 25.89 | 51.08 | 49.76 | 45.35 | 55.93 |
| Tyrosine | 52.52 | 38.35 | 46.92 | 49.01 | 39.17 | 50.06 |
| Phenylalanine | 53.75 | 40.53 | 49.35 | 50.06 | 33.55 | 45.53 |
| Lysine | 56.39 | 45.02 | 53.26 | 52.70 | 35.86 | 42.72 |
| Histidine | 45.05 | 32.83 | 54.75 | 42.03 | 46.28 | 54.05 |
| Arginine | 66.22 | 43.21 | 62.52 | 48.22 | 54.83 | 56.66 |
| Tryptophan | 50.66 | 39.36 | 45.34 | 48.62 | 36.52 | 41.94 |

Additional data was generated for the different feed products as shown in the table below.

TABLE IX

Protein and Fat Data

| Sample ID | Crude Fiber (Dry Basis) | Fat-Ankom_Fat Dry Basis | Fat-Ankom_Fat As-Is | LECO_Ave % Protein Dry Basis | LECO_Protein AS IS |
|---|---|---|---|---|---|
| SCP-A | 0.15 | 0.80 | 0.76 | 45.28 | 43.30 |
| SCP-B | 0.08 | 0.82 | 0.80 | 38.31 | 37.41 |
| SCP-C | 1.81 | 9.39 | 9.14 | 41.23 | 40.13 |
| SCP-1 | 0.18 | 0.99 | 0.97 | 43.75 | 42.94 |
| SCP-2(a) | 0.90 | 5.71 | 5.47 | 40.96 | 39.25 |
| SCP-2(b) | 1.23 | 5.13 | 4.93 | 40.21 | 38.60 |
| SCP-3 | 1.18 | 6.43 | 6.25 | 48.18 | 46.83 |

The products SCP-A, SCP-B, and SCP-1, were produced using the processes described with reference to FIGS. 4, 5 and the SCP process. The products, SCP-C, SCP-2, and SCP-3 were produced using the processes described with reference to FIGS. 13-15.

Animal feed trials were conducted, where experimental diets were fed to fish. The diets were isonitrogenous, iso-energetic, and contained similar amounts of lysine, methionine, and threonine. Table X. shows the data below for the products produced from these processes.

TABLE X

Diets Fed to Fish (% as-fed basis)

| Ingredient | Negative Control | 406 | 510-A | 510-B | SCP-1 | SCP-2 | SCP-3 | Positive Control |
|---|---|---|---|---|---|---|---|---|
| Wheat midds | 8.8 | 8.0 | 8.0 | 8.0 | 8.0 | 8.0 | 8.9 | 16.9 |
| Wheat grain | 11.0 | 15.0 | 15.0 | 12.7 | 12.2 | 12.1 | 14.6 | 16.0 |
| Poultry byproduct meal | 20.6 | 19.1 | 19.1 | 20.6 | 20.0 | 21.0 | 18.0 | 23.0 |

TABLE X-continued

| | Diets Fed to Fish (% as-fed basis) | | | | | | | |
|---|---|---|---|---|---|---|---|---|
| Ingredient | Negative Control | 406 | 510-A | 510-B | SCP-1 | SCP-2 | SCP-3 | Positive Control |
| Feather meal | 7.5 | 6.5 | 6.5 | 7.5 | 6.5 | 6.5 | 6.0 | 8.0 |
| Fish oil | 12.0 | 10.0 | 10.0 | 10.0 | 12.0 | 11.0 | 11.0 | 10.5 |
| Fish meal | 12.0 | 12.0 | 12.0 | 12.0 | 12.0 | 12.0 | 12.0 | 15.0 |
| Blood meal | 2.0 | 2.0 | 2.0 | 2.0 | 2.0 | 2.0 | 2.0 | 5.0 |
| Vitamin premix | 1.3 | 1.3 | 1.3 | 1.3 | 1.3 | 1.3 | 1.3 | 1.3 |
| Lysine | 1.8 | 2.4 | 2.4 | 24 | 2.3 | 2.4 | 2.5 | 1.8 |
| Trace mineral premix | 0.8 | 0.8 | 0.8 | 0.8 | 0.8 | 0.8 | 0.8 | 0.8 |
| Monocalcium phosphate | 1.0 | 1.0 | 1.0 | 1.0 | 1.0 | 1.0 | 1.0 | 0.5 |
| Choline | 0.6 | 0.6 | 0.6 | 0.6 | 0.6 | 0.6 | 0.6 | 0.6 |
| Methionine | 0.5 | 0.8 | 0.8 | 0.5 | 0.8 | 0.8 | 0.8 | 0.5 |
| Threonine | 0.1 | 0.5 | 0.5 | 0.5 | 0.5 | 0.5 | 0.5 | 0.0 |
| Ascorbic acid | 0.2 | 0.2 | 0.2 | 0.2 | 0.2 | 0.2 | 0.2 | 0.2 |
| Experimental Yeast treatment[b] | 20.0 | 20.0 | 20.0 | 20.0 | 20.0 | 20.0 | 20.0 | — |

The positive control is "The Standard" diet from Nutrient Requirements of Fish and Shrimp, by the National Academies Press, 2011. The negative control diet includes a commercial yeast source that is neither spray dried nor hydrolyzed enzymatically.

The fish trial took over 63 days using the above products shown in Table XI. The results from the fish trial are shown in Table XI.

TABLE XI

Fish Trial Results

| Treatment | Feed Offered (g total/tank) | Weight Gain (g/fish) | Specific Growth Rate (% BW/day) | Feed Conversion Rate (daily g feed/g fish weight gain) |
|---|---|---|---|---|
| Negative Control | 1688$^a$ | 58.2$^{abc}$ | 1.91$^{ab}$ | 1.15$^{ab}$ |
| 406 | 1813$^{bc}$ | 58.8$^{ab}$ | 1.95$^b$ | 1.18$^{ab}$ |
| 510-A | 1740$^{ab}$ | 55.0$^c$ | 1.83$^a$ | 1.27$^c$ |
| 510-B | 2119$^d$ | 73.3$^d$ | 2.32$^e$ | 1.02$^d$ |
| SCP-1 | 1902$^{ce}$ | 61.0$^{ce}$ | 2.00$^{ab}$ | 1.19$^b$ |
| SCP-2 | 1949$^e$ | 64.0$^e$ | 2.09$^d$ | 1.14$^a$ |
| SCP-3 | 1974$^e$ | 69.5$^e$ | 2.22$^e$ | 1.04$^d$ |
| Positive Control | 1986$^e$ | 75.5$^d$ | 2.40$^e$ | 0.93$^e$ |
| Std Error of the Mean | 31 | 2.2 | 0.03 | 0.01 |

Means in each column with unlike superscripts differ (P < 0.05)

Turning to column 1, the data indicate that 510-B demonstrated the highest feed intake at 2119 g total/tank. Turning to column 3, the specific growth rate was highest for both the positive control and Product 510-B at 2.32% BW/day (i.e., these two treatments did not differ significantly). Although the feed conversion of 510-B at 1.02 daily g feed/g fish weight gain was significantly higher than the positive control (column 4), it is overall acceptable by industry standard. Thus, the data indicate 510-B did well in the fish trials.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A method for separating components in a process stream, the method comprising:
    receiving a process stream having a mixture of components of one or more liquids and one or more solids;
    adding a non-condensable media to the mixture to change a density of each of the components, wherein the non-condensable media is selected from the group consisting of air, carbon dioxide, nitrogen, oxygen, and combinations thereof;
    separating the one or more liquids and the one or more solids of the process stream using an apparatus selected from the following:
    a sedicanter centrifuge, a decanter centrifuge, a disk stack centrifuge, and combinations thereof, to provide a separated solids stream and a separated liquids stream;
    separating the separated liquids stream with a first separation device to provide a light emulsion phase and a heavy phase with suspended solids;
    separating the heavy phase with suspended solids with a second separation device to provide a clarified heavy phase and a light phase concentrate, wherein the clarified heavy phase comprises 1% to 30% fat and 0.7% to 70% available oil;
    reducing viscosity of the heavy phase with suspended solids by adding a chemical to the heavy phase with suspended solids; and
    separating the light emulsion phase with a mechanical separation device to produce oil, heavy phase solids, and heavy phase liquids.

2. The method of claim 1, wherein the first separation device is selected from the group consisting of a dissolved air floatation device, an open tank dissolved air floatation device, a dispersed air flotation device, an electrolysis flotation device, and combinations thereof.

3. The method of claim 1, wherein the second separation device is selected from the group consisting of a dissolved air floatation device, an open tank dissolved air floatation device, and combinations thereof.

4. The method of claim 1, further comprising adding a second non-condensable media to the separated liquids stream before the separation in the first separation device, wherein the second non-condensable media is selected from the group consisting of air, carbon dioxide, nitrogen, oxygen, and combinations thereof.

5. The method of claim 1, wherein the chemical is selected from the group consisting of a polymer, a synthetic water-soluble polymer, a dry polymer, an emulsion polymer, a latex polymer, a dispersion polymer, a cationic flocculant, a cationic coagulant, an anionic flocculant, or an anionic coagulant, and combinations thereof.

6. The method of claim 1, selecting the mechanical separation device is from the group consisting of a rotary drum vacuum filter, a dynamic cross-flow filtration device, a cross-flow filtration device, a filtering centrifuge, and combinations thereof.

\* \* \* \* \*

UNITED STATES PATENT AND TRADEMARK OFFICE
CERTIFICATE OF CORRECTION

PATENT NO. : 11,998,026 B2
APPLICATION NO. : 16/624831
DATED : June 4, 2024
INVENTOR(S) : Gallop et al.

It is certified that error appears in the above-identified patent and that said Letters Patent is hereby corrected as shown below:

In the Claims

In Column 28, Line 52, in Claim 1, delete "70%" and insert --20%-- therefor

Signed and Sealed this
Tenth Day of December, 2024

Katherine Kelly Vidal
*Director of the United States Patent and Trademark Office*